United States Patent [19]
Engvall et al.

[11] Patent Number: 5,780,244
[45] Date of Patent: Jul. 14, 1998

[54] CHANGES IN LAMININ SUBUNIT COMPOSITION ARE DIAGNOSTIC OF FUKUYAMA CONGENITAL MUSCULAR DYSTROPHY

[75] Inventors: Eva Engvall, Rancho Santa Fe, Calif.; Kiichi Arahata, Tokyo, Japan

[73] Assignee: La Jolla Cancer Research Foundation, La Jolla, Calif.

[21] Appl. No.: 196,828

[22] Filed: Feb. 14, 1994

Related U.S. Application Data

[63] Continuation-in-part of Ser. No. 127,589, Sep. 27, 1993, abandoned.

[51] Int. Cl.⁶ ................................................. G01N 33/53
[52] U.S. Cl. .................... 435/7.21; 435/7.1; 435/7.94; 435/7.95; 435/960; 436/811
[58] Field of Search ............................ 435/7.21, 7.1, 435/960, 975, 7.94, 7.95; 436/63, 811; 530/388.2

[56] References Cited

U.S. PATENT DOCUMENTS

| | | | |
|---|---|---|---|
| 5,308,752 | 5/1994 | Campbell et al. | 435/7.21 |
| 5,340,718 | 8/1994 | Ishiguro et al. | 435/7.1 |

OTHER PUBLICATIONS

Leivo, I. and Engvall, E. "Merosin, a Protein Specific for Basement Membranes of Schwann Cells, Striated Muscle, and Trophoblast, is Expressed Late in Nerve and Muscle Development." Proc. Natl. Acad. Sci. USA. 85:1544–1548 (1988).

Wewer, U.M. et al., "Laminin A, B1, B2, S and M Subunits in the Postnatal Rat Liver Development and After Partial Hepatectomy." Labor. Invest. 66:378–389 (1992).

Matsumura, K. et al., "Abnormal Expression of Dystrophin–Associated Proteins in Fukuyama–type Congenital Muscular Dystrophy." Lancet. 341:521–522 (1993).

Arikawa, E. et al., "Immunocytochemical Analysis of Dystrophin in Congenital Muscular Dystrophy." J. Neurol. Sci. 105:79–87 (1991).

Porter, G.A., et al., "Dystrophin Colocalizes with β–Spectrin in Distinct Subsarcolemmal Domains in Mammalian Skeletal Muscle." J. Cell Biol. 117:997–1005 (1992).

Beggs, A.H. et al., "Possible Influences on the Expression of X Chromosome–linked Dystrophin Abnormalitites by Heterozygosity for Autosomal Recessive Fukuyama Congenital Muscular Dystrophy." Proc. Natl. Acad. Sci. USA. 89:623–627 (1992).

Ehrig, Karin et al., "Merosin, A Tissue–specific Basement Membrane Protein, is a Laminin–like Protein." Proc. Natl. Acad. Sci. USA. 87:3264–3268 (1990).

Prigojin, Hagit et al., "Detection of Duchenne Muscular Dystrophy Gene Products in Amniotic Fluid and Chorionic Villus Sampling Cells." FEBS 335:223–230 (1993).

(List continued on next page.)

*Primary Examiner*—Christina Y. Chan
*Assistant Examiner*—James L. Grun
*Attorney, Agent, or Firm*—Campbell & Flores LLP

[57] ABSTRACT

The present invention relates to a method for detecting altered expression or localization of a cytoskeleton/basal lamina protein in a tissue sample obtained from an individual, wherein the altered expression or localization are associated with a muscular dystrophy such as Fukuyama congenital muscular dystrophy (FCMD). The invention provides an immunohistochemical method for detecting the expression and localization in a tissue, such as muscle, of laminin M (merosin), which is a protein component of the basal lamina, wherein certain defined changes are diagnostic of individuals predisposed to FCMD. The invention also provides a prenatal diagnostic screening procedure, using a tissue such as placenta, wherein the screening procedure can identify an individual predisposed to FCMD. The invention further provides methods for identifying an individual predisposed to other muscular dystrophies such as Walker-Warburg Syndrome (WWS) and muscle-eye-brain disease of the Finnish type (MEB).

7 Claims, 12 Drawing Sheets

OTHER PUBLICATIONS

Sunada, Yoshihide, et al., "Deficiency of Merosin in Dystrophic dy Mice and Genetic Linkage of Laminin M Chain Gene to dy Locus." J. Biol. Chem. 269:13729–13732 (1994).

Hoffman et al, 1988. Characterization of dystrophin in muscle–biopsy specimens from patients with Duchenne's or Becker's muscular dystrophy. N Eng J Med 318:1363–8.

Ervasti, et al., 1990. Deficiency of a glycoprotein component of the dystrophic complex in dystrophic muscle. Nature 345:315–319.

Arahata et al, Dec 1993. Laminin in animal models for muscular dystrophy... Proc. Japan Academy, vol. 69, Series B, 259–264.

Tomé et al, 1994. Congenital muscular dystrophy with merosin deficiency. C.R. Acad. Sci. Paris, Series III, Sciences de la vie/Life Sciences 317(4):351–357.

Hantai, Daniel et al., "Fibronectin, Laminin, Type I, III and IV Collagens in Duchenne's Muscular Dystrophy, Congenital Muscular Dystrophies and Congenital Myopathies: An Immunocytochemical Study." Connective Tissue Research 13:273–281 (1985).

Clarke, Mark S.F. et al., "Loss of Cytoplasmic Basic Fibroblast Growth Factor from Physiologically Wounded Myofibers of Normal and Dystrophic Muscle." J. Cell Science. 106:121–133 (1993).

Bertolotto, Antonio et al., "Laminin and Fibronectin Distribution in Normal and Pathological Human Muscle." J. Neurological Sciences. 60:377–382 (1983).

Hayashi, Yukiko K. et al., "Abnormal Localization of Laminin Subunits in Muscular Dystrophies." J. Neurological Sciences. 119:53–64 (1993).

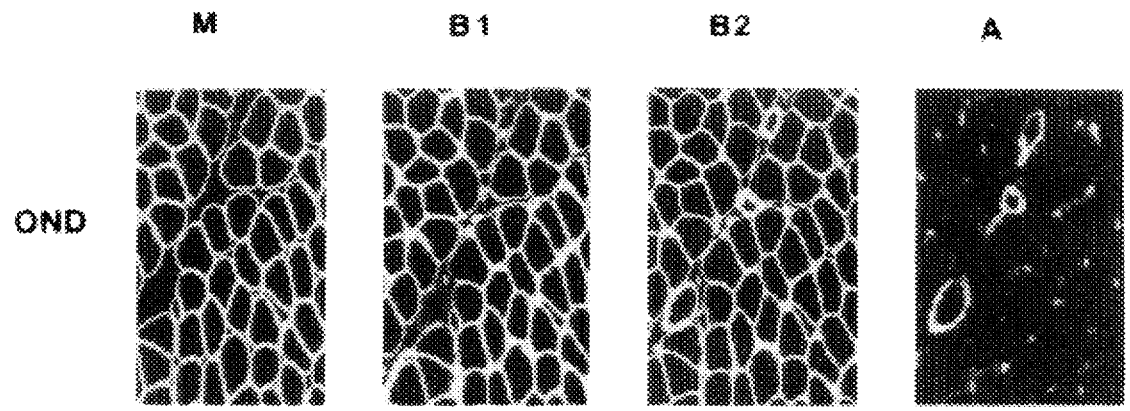
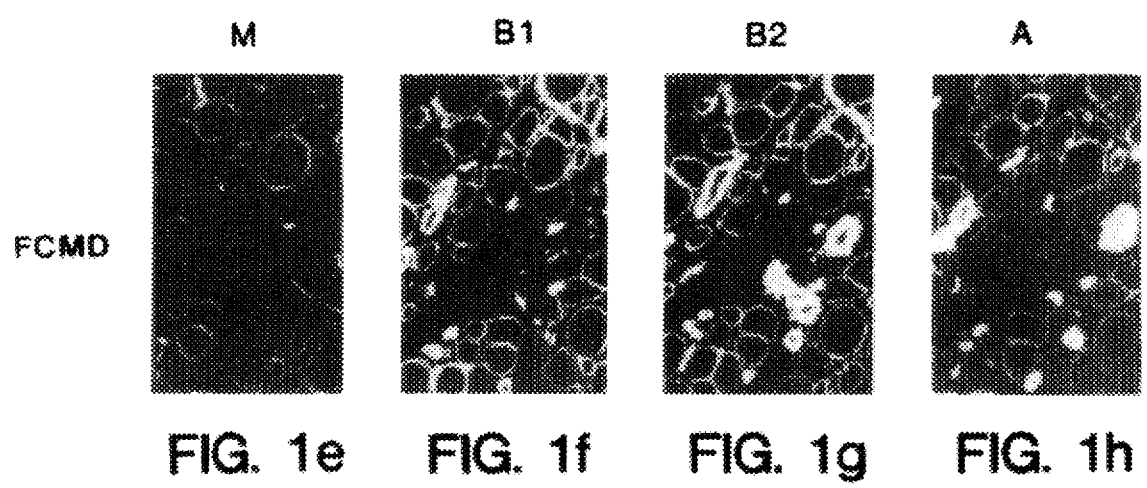

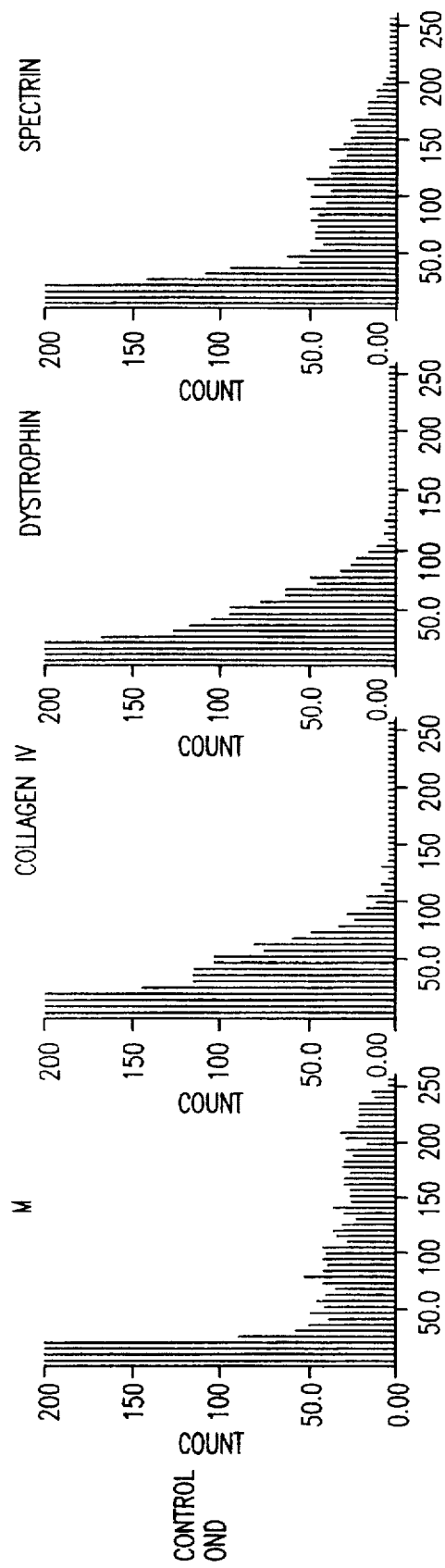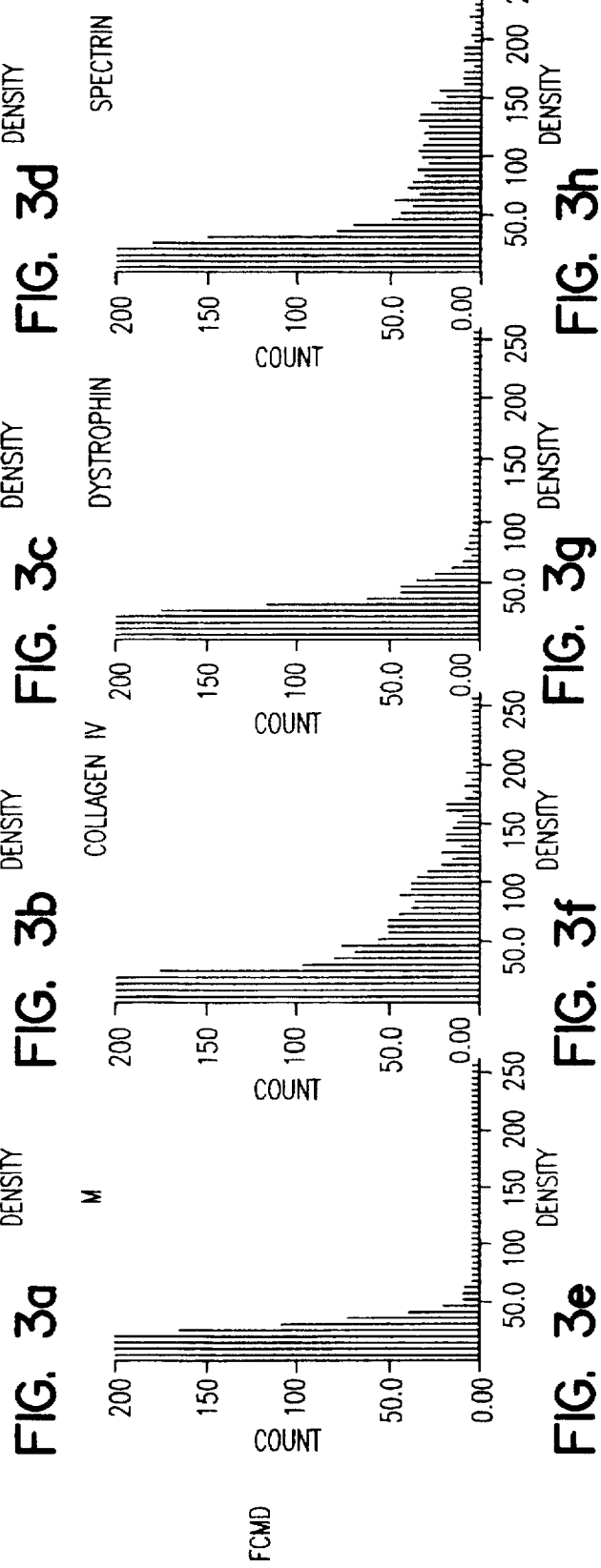

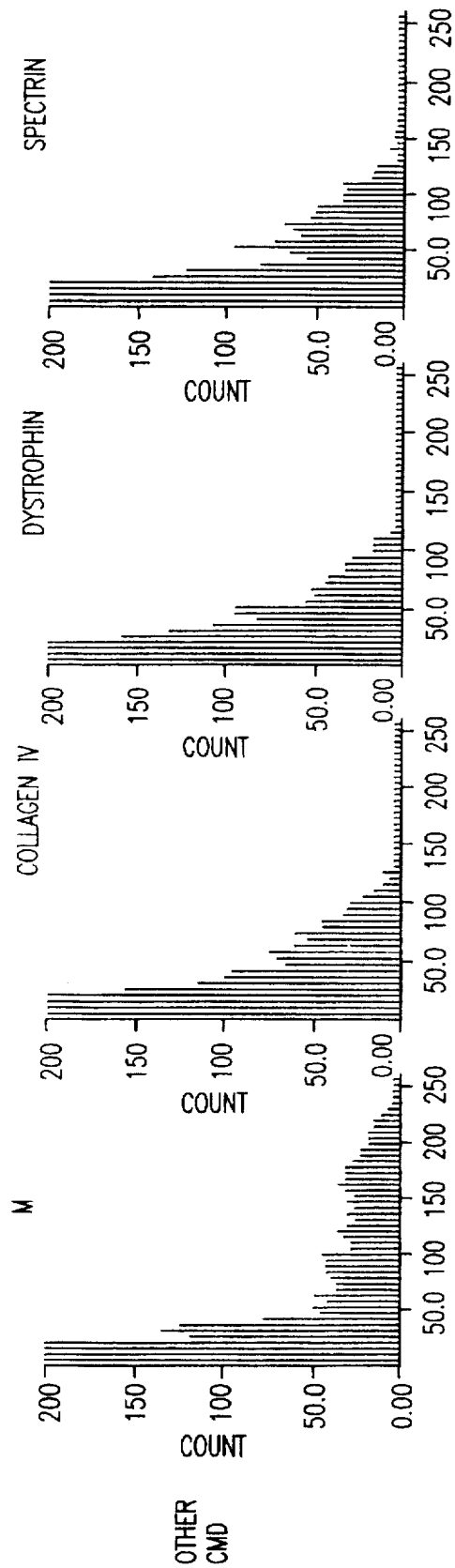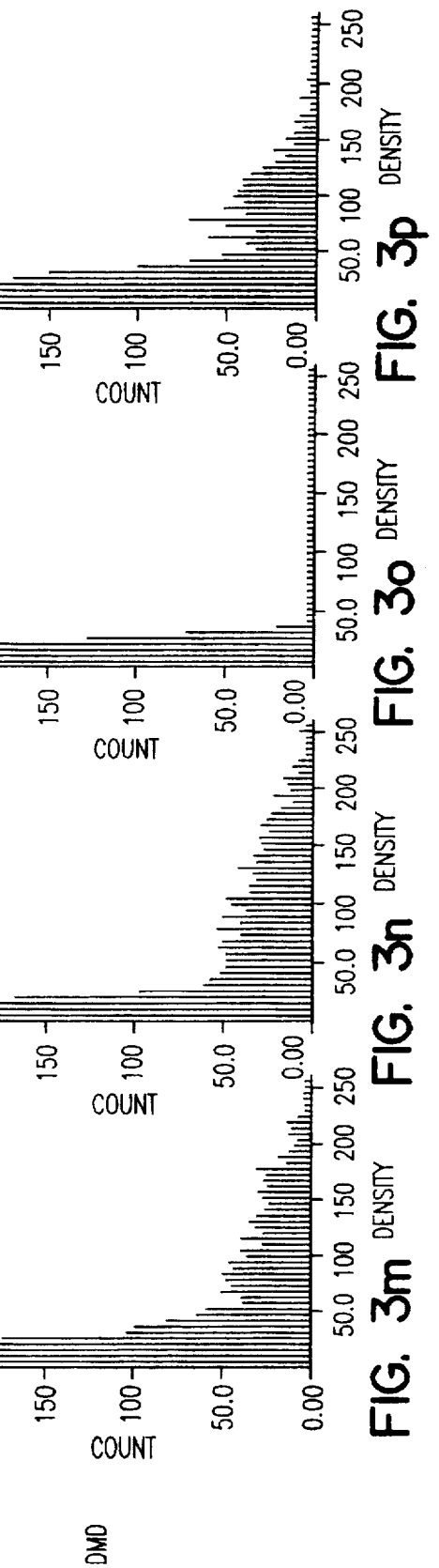

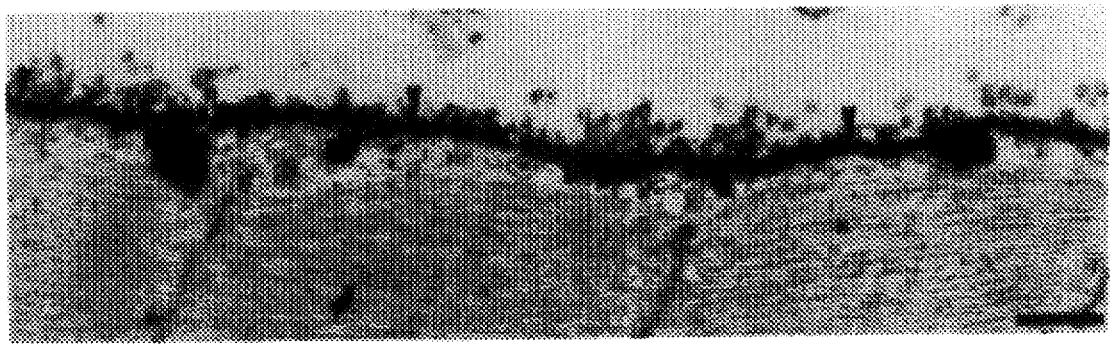
FIG. 8A
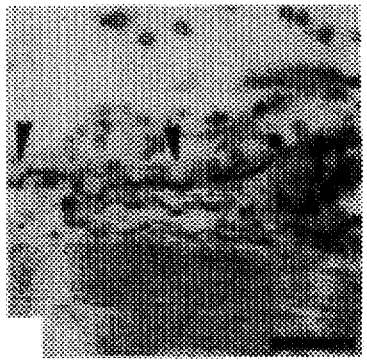 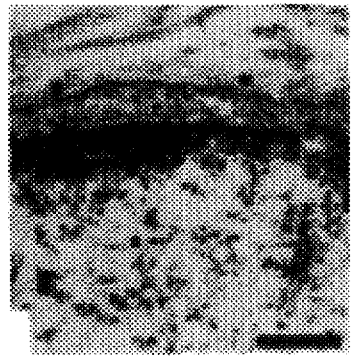 
FIG. 8B  FIG. 8C  FIG. 8D

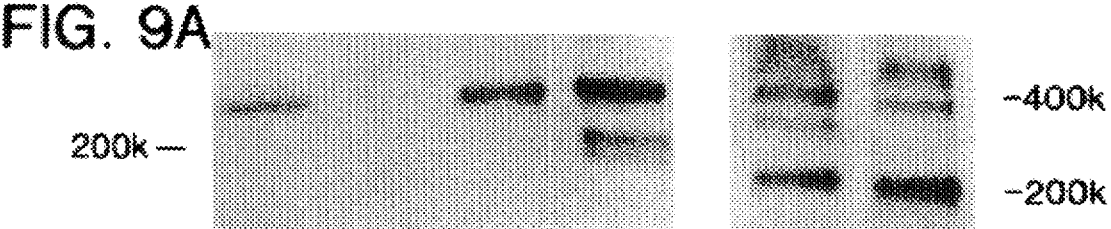
FIG. 9A
FIG. 9B
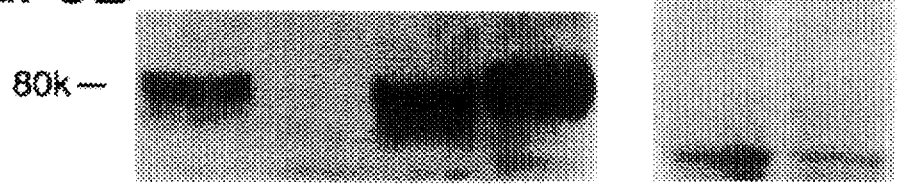
FIG. 9C 5,780,244

1

CHANGES IN LAMININ SUBUNIT COMPOSITION ARE DIAGNOSTIC OF FUKUYAMA CONGENITAL MUSCULAR DYSTROPHY

This application is a continuation-in-part of U.S. Ser. No. 08/127,589, filed Sep. 27, 1993, now abandoned, the contents of which is incorporated herein by reference.

This work was supported by grant number CA 28896 awarded by the National Cancer Institute. The United States government has certain rights in this invention.

FIELD OF THE INVENTION

This invention relates generally to the field of medicine and more specifically to methods for detecting changes in the expression of laminin M protein and of M chain mRNA that are diagnostic of Fukuyama congenital muscular dystrophy (FCMD). The invention further relates to methods of identifying agents that can reduce or prevent the symptoms associated with FCMD and to methods of treating an FCMD patient.

BACKGROUND OF THE INVENTION

The basal lamina of muscle fibers is a specialized extracellular matrix that has a static structure that contributes to the proper migration, proliferation and regeneration of myogenic cells during development or after injury or tissue grafting (Alberts et al., *Molecular Biology of the Cell* (Garland Publ., Inc. 1989); Sanes et al., *Myology* (McGraw-Hill Book Co., NY, 1986); Martin, G. R., *Ann. Rev. Cell Biol.* 3:37–85 (1987); Alameddine et al., *Neuromusc. Dis.* 1:143–152 (1991)). The components of the basal lamina include laminin, type IV collagen, fibronectin and heparan-sulfate proteoglycan. The large laminin protein, which has a molecular weight of approximately 850 kilodaltons (kdal), is a heterotrimer consisting of two smaller chains (B1, S or B2) and one larger chain (A or M) which are arranged in the shape of a cross. Thus, laminin trimers have various structures such as A-B1-B2, M-B1-B2, A-S-B2 and M-S-B2. Other laminins such as kalinin and K-laminin contain an A chain homolog, designated K (Marinkovich et al., *J. Cell Biol.* 119:695–703 (1992).

Laminin is found adjacent to the plasma membrane of muscle fibers, where its multiple functional domains bind type IV collagen, proteoglycans and laminin receptor proteins, such as integrins (Hynes and Lander, *Cell* 68:303–322 (1992)) and the 156 kdal dystrophin-associated glycoprotein (DAG) (Ibraghimov-Beskrovnaya et al., *Nature* 355:696–702 (1992)), which are present on the plasma membrane of the muscle fibers. The various laminin isoforms can be either ubiquitously expressed or tissue-specific (Leivo and Engvall, *Proc. Natl. Acad. Sci. USA* 85:1544–1548 (1988); Ehrig et al., *Proc. Natl. Acad. Sci. USA* 87:3264–3268 (1990); Sanes et al., *J. Cell Biol.* 111:1685–1699 (1990)). For example, laminin M (merosin) contains an M chain subunit that is specific for striated muscle, Schwann cells and trophoblast, where it replaces the "A" subunit in the ubiquitous non-muscle laminin polyprotein (Leivo and Engvall (1988); Wewer et al., *Lab. Invest.* 66:378–389 (1992)).

The expression and distribution of laminin, collagen and other extracellular matrix in normal and pathological muscles have been examined (see, for example, Rampoldi et al., *Eur. J. Cell Biol.* 42:27–34 (1986); Hantai et al., *Connective Tiss. Res.* 13:273–281 (1985)). Although various studies indicate that a prominent increase of type III and type I collagen and/or fibronectin occurs in the perimysial and endomysial muscle tissue of patients with muscular dystrophies and inflammatory myopathies, no disease-specific accumulation of these extracellular matrix proteins has been identified. Similarly, basal lamina-associated type IV collagen and laminin proteins appear to be normal (Bertolotto et al., *J. Neuro. Sci.* 60:377–382 (1983)) or do not show significant changes.

Primary deficiencies of protein components of the membrane cytoskeleton of muscle fibers include dystrophin and dystrophin-glycoprotein complexes, which are detected in Duchenne and Becker Muscular Dystrophy (Ibraghimov-Beskrovnaya et al. (1992); Ervasti et al., *Nature* 345:315–319 (1990); Ervasti and Campbell, *Cell* 66:1121–1131 (1991); Yoshida and Ozawa, *J. Biochem.* 108:748–752 (1990)). Secondary deficiencies also occur. For example, the laminin-binding 156 kdal DAG is markedly reduced in human Duchenne muscular dystrophy (DMD) and in muscle obtained from mdx mice, which are the murine equivalent of Duchenne/Becker muscular dystrophy in humans (Ervasti et al. (1990)). The lack of dystrophin protein in mdx mouse is due to a mutation in the dystrophin gene (Bulfield 1984), Hoffman et al., 1987). Although the mdx mouse has a much milder phenotype than human patients with dystrophin defects has provided a useful model system for studying the molecular mechanisms responsible for DMD in humans.

Other forms of muscular dystrophy in humans are known. For example, a deficiency of a 50 kdal DAG component of the membrane cytoskeleton was observed in an autosomal recessive form of muscular dystrophy that is prevalent in North Africa (Matsumura et al., *Nature* 359:320–322 (1992) ). Fukuyama congenital muscular dystrophy (FCMD) is an autosomal recessive form of congenital muscular dystrophy that is endemic to Japan and has an incidence of 6.9–11.9 per 100,000 births. FCMD is characterized by progressive muscle wasting and dystrophic muscle pathology. In addition, central nervous system involvement results in profound mental retardation associated with abnormal brain pathology such as neuronal and glial heterotopias (Kamoshita et al., *Arch. Neurol.* 33:513–516 (1976); Stern and Manson, *Devel. Med. Child Neurol.* 32:808–813 (1988); Fukuyama et al., *Brain Devel.* 13:1–29 (1981)). Other forms of muscular dystrophy such as muscle-eye-brain disease of the Finnish type (MEB) and Walker-Warburg Syndrome (WWS) also occur as autosomal recessive diseases and may be a result of the same genetic defect as FCMD ((Cook et al., *J. Child. Neurol.* 7:S51–63 (1992); Osawa et al., *Acta Paediatr.* (Japan) 33:261–269 (1991); Lenard, H. G., *Acta Paediatr.* (Japan) 33:256–260 (1991); Miller et al., *Acta Neuropathol.* (Berlin) 82:234–238 (1991); Yoshioka et al., *Brain Devel.* 12:423–426 (1990)).

No methods are available for identifying individuals in a population who are predisposed to FCMD, WWS or MEB and members of families having relatives with such a congenital muscular dystrophy must live with the knowledge that they may ultimately develop clinical symptoms of the disease or pass the disease to their children. Furthermore, no animal model is available for an autosomal recessive muscular dystrophy such as FCMD. The identification of such a model would provide a system that can be manipulated to identify and develop effective methods of alleviating the suffering caused by these diseases. Thus, a need exists for simple, efficient methods of identifying individuals predisposed to developing Fukuyama congenital muscular dystrophy and effective methods for treating FCMD patients. The present invention satisfies this need and provides related advantages as well.

SUMMARY OF THE INVENTION

The present invention provides methods for detecting changes in the basal lamina of individuals predisposed to a muscular dystrophy such as Fukuyama congenital muscular dystrophy (FCMD). The invention provides, for example, an immunohistochemical method for detecting the expression and localization of laminin M in a tissue, wherein identifiable changes in the expression and localization of laminin M are diagnostic of FCMD. The invention further provides methods of nucleic acid hybridization for detecting the expression of M chain mRNA in a tissue, wherein identifiable changes in the expression of M chain mRNA levels are diagnostic of FCMD. The invention also provides a prenatal diagnostic screening procedure using a tissue such as placenta or fetal muscle, wherein the screening procedure is useful for identifying an individual predisposed to FCMD. The invention further provides methods for identifying an individual predisposed to other muscular dystrophies such as Walker-Warburg Syndrome (WWS) and muscle-eye-brain disease of the Finnish type (MEB). The invention also provides a method of screening agents that may be useful for treating FCMD patients, wherein the screening method utilizes the dy/dy mouse model of FCMD. The invention further provides diagnostic assay kits useful for identifying an individual predisposed to a muscular dystrophy.

BRIEF DESCRIPTION OF THE DRAWINGS

FIGS. 3.a. to 3.p. Bar graphs show the results of quantitative densitometric analysis for each immunoreaction using the IBAS system (Zeiss). Muscles from control OND (FIGS. 3a–3d), FCMD (FIGS. 3e–3h), other CMD (FIGS. 3i–3l) and DMD (FIGS. 3m–3p) patients immunostained for laminin M (FIGS. 3a, 3e, 3i and 3m), type IV collagen (FIGS. 3b, 3f, 3j and 3n) dystrophin (FIGS. 3c, 3g, 3k and 3o) and spectrin (FIGS. 3d, 3h, 3l and 3p). A grey value of less than 40 on the histogram indicates background intensity. Dystrophin is undetectable in DMD (FIG. 3o) and a remarkable reduction of laminin M is observed in FCMD muscle (FIG. 3e). Note: Immunolabelling intensity per assigned region (56006.25 µm$^2$) and per unit plasma membrane length (1.0 µm) are reported in Table 4.a. and Table 4.b., respectively.

FIG. 8.a. Adjacent sections of skeletal leg muscle from 5 week old dystrophic (dy/dy) and normal (+/?) mice were stained with affinity purified anti-M chain antibody (20 µg/ml) or with polyspecific anti-laminin antiserum (1:200). The dystrophic dy/dy mouse showed a complete lack of reactivity in the basement membranes of muscle fibers and peripheral nerve (N) with the M chain-specific antibodies, while normal reactivity was detected with the polyspecific anti-laminin antiserum.

FIG. 8.b. Sections of skeletal muscle stained with antiserum to type IV collagen and monoclonal antibodies to perlecan (undiluted hybridoma culture medium) showed similar staining intensities in normal and dystrophic mice.

FIG. 9A–9D. Transmission electron microscopy of skeletal muscle from 8 week old normal (FIG. 9A) and dystrophic (FIGS. 9B–9D) mice. Arrows indicate basement membrane and asterisks show areas where the basement membrane is absent. Magnifications: A, 25,000×; B, 45,000×; C, 36,000×; D, 43,000×.

FIGS. 10.a. to 10.c. Extracts of skeletal muscle from dystrophic and normal mice were fractionated by SDS-PAGE and protein bands were transferred to Immobilon filters and immunostained using various antibodies.

(FIG. 10c) Polyspecific antiserum to human placental laminin. The dystrophic mice lack both the 300 kDa N-terminal segment (FIGS. 10a and 10c) and the 80 kDa C-terminal segment (FIG. 10b). The dystrophic mice contain laminin heavy (400 kDa) and light (200 kDa) chain in apparently normal amounts (FIG. 10c). wt=wild type. HumM=human laminin M isolated from placenta.

FIG. 12. RT-PCR amplification of a segment of poly $A^+$ RNA from skeletal muscle of normal and dystrophic mice shows that some M chain mRNA is present in the dystrophic mouse. ("NC" indicates "negative control," i.e., sample without RNA).

DETAILED DESCRIPTION OF THE INVENTION

Figures 1I, 1J, 1K, 1L:
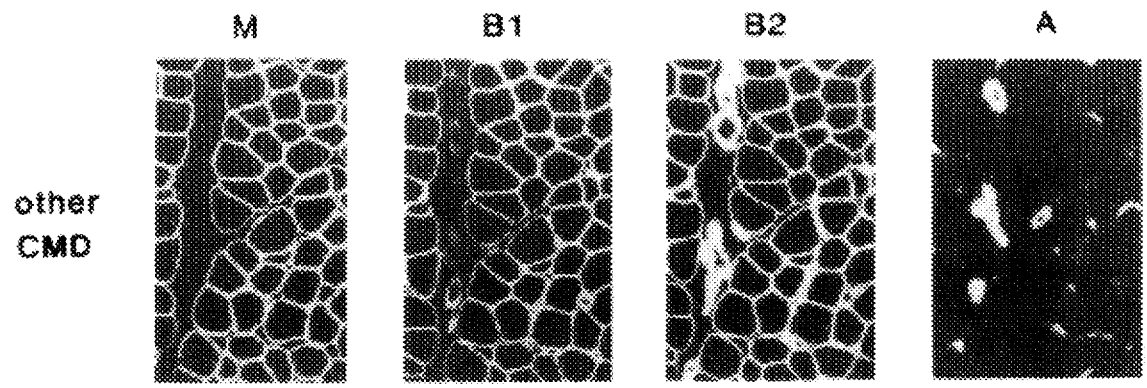
FIGS. 1.a. to 1.p. Consecutive frozen sections of biopsied skeletal muscles from control OND (FIGS. 1a–1d), FCMD (FIGS. 1e–1h), other CMD (FIGS. 1i–1l) and DMD (FIGS. 1m–1p) patients immunostained for laminin M (FIGS. 1a, 1e, 1i, 1m), laminin B1 (FIGS. 1b, 1f, 1j, 1n), laminin B2 (FIGS. 1c, 1g, 1k, 1o) or laminin A (FIGS. 1d, 1h, 1l, 1p). Note the faint, deranged pattern of immunoreactivity observed for laminin M, laminin B1 and laminin B2 at the muscle fiber basal lamina in samples obtained from FCMD patients (FIGS. 1e, 1f, 1g). In contrast, strong, clear immunoreactivity for these laminin subunits is observed in the basal lamina of samples obtained from the other groups of subjects. Laminin A is not detected in OND or in other CMD muscles but is observed in FCMD and DMD. Intramuscular blood vessels are not reactive for laminin M, whereas they are immunoreactive for laminin B1, laminin B2 and laminin A in all samples examined. Magnification ×215.

The present invention provides methods for detecting changes in the basal lamina of individuals predisposed to a congenital muscular dystrophy such Fukuyama congenital muscular dystrophy (FCMD). The invention provides, for example, an immunohistochemical method for detecting the expression and localization of laminin M in a suitable tissue sample such as muscle or peripheral nerve obtained from an individual suspected of being predisposed to FCMD, wherein identifiable changes in the expression and localization of laminin M identify the individual as being predisposed to FCMD. The invention further provides methods of nucleic acid hybridization for detecting the expression of M chain mRNA in a tissue, wherein identifiable changes in the expression of M chain mRNA levels are diagnostic of FCMD. The invention also provides a prenatal diagnostic screening procedure using a tissue such as placenta or fetal muscle, wherein the screening procedure is useful for identifying an individual predisposed to FCMD, and methods for identifying an individual predisposed to other muscular dystrophies such as WWS and MEB, which can occur as a result of the same genetic defect observed in FCMD patients. The invention also provides a method of identifying agents that can be useful for treating FCMD patients, wherein the method utilizes a mouse model system of FCMD. The invention further provides diagnostic assay kits useful for identifying an individual predisposed to a muscular dystrophy.

Identification of an individual having altered expression and localization of laminin M protein or altered expression of M chain mRNA can indicate that the individual is predisposed to exhibiting the clinical symptoms of a congenital muscular dystrophy. For example, the identification of altered expression of M chain mRNA in a tissue sample obtained from a fetus suspected of being predisposed to FCMD can indicate that the individual is predisposed to exhibiting the clinical symptoms associated with FCMD after birth. In addition, the identification of such altered expression in an individual can indicate that the person is predisposed to exhibiting a late onset form of a muscular dystrophy. Such information is useful in allowing the predisposed individual an opportunity to make adequate preparations, for example, for future care. Prenatal diagnosis of an individual predisposed, for example, to FCMD, WWS or MEB is particularly valuable as this information allows the parents of the predisposed individual to make an informed decision as to how best to proceed with the pregnancy.

One aspect of the present invention provides a systematic qualitative and quantitative analysis of the major protein components of the basal lamina (laminin A, B1, B2, M and type IV collagen) and the membrane cytoskeleton (dystrophin and spectrin) of muscle fibers. Special interest is directed to laminin M, which is a specific component of striated muscle, Schwann cells and trophoblast (Leivo and Engvall, Proc. Natl. Acad. Sci. USA 85:1544–1548 (1988), which is incorporated herein by reference). The basal lamina of control muscle fibers and of a tissue sample obtained from normal human trophoblast showed strong immunostaining for laminin M, laminin B1 and laminin B2 subunits and for type IV collagen, as did most degenerating, regenerating or necrotic muscle fibers. In contrast, immunostaining for laminin M protein in muscle samples obtained from FCMD patients showed significantly reduced immunostaining intensity and an altered immunostaining pattern. Furthermore, one FCMD patient had no detectable laminin M protein but was positive for laminin B1 and laminin B2.

Immunoreactivity of laminin B1 and laminin B2 also were significantly abnormal in FCMD muscle and showed reduced immunostaining intensity and an altered immunostaining pattern. However, these changes were less prominent than the changes observed for laminin M protein in FCMD muscle. In contrast to the altered immunoreactivity of laminin M in muscle from FCMD patients, the basal lamina of capillary, neuromuscular junction, intramuscular peripheral nerve and most intrafusal muscle fibers immunostained clearly for laminin A, laminin B1 and laminin B2.

Immunoreactivity studies of type IV collagen, dystrophin and spectrin in muscle samples from FCMD patients produced different results depending on the method of evaluation. Subjective evaluation of immunostaining patterns showed an increased percentage of total abnormal fibers (83% type IV collagen, 26% dystrophin, 20% spectrin) (Table 3, below). However, quantitation of fluorescence intensity did not reveal any significant abnormality in immunoreactivity (Tables 4.a. and 4.b., below). Thus, an abnormal immunostaining pattern for type IV collagen, dystrophin or spectrin does not necessarily correlate with a reduction of immunolabelling intensity. This result indicates that changes in the localization pattern rather than expression of these proteins occur in the muscles of FCMD patients and that a structural alteration of the basal lamina is involved, at least in part, in the pathophysiology of muscle fiber damage in FCMD.

Although laminin M showed the most striking and consistent changes in FCMD patients both qualitatively (FIGS. 1 and 2 and Table 3, below) and quantitatively (FIG. 3 and Tables 4.a. and 4.b., below), changes of the laminin A subunit on diseased muscles also were noted. Laminin A was undetectable in the basal lamina of control muscle but was detected in approximately 90% of FCMD and DMD muscle fibers (see FIGS. 1h and 1p, and FIGS. 4f and 4i). Interestingly, antibodies to laminin A selectively stained dystrophin negative, normal-appearing muscle fibers of a DMD carrier, thus revealing a reverse mosaic pattern (FIG. 5). The sample did show, however, the presence of a few laminin A-positive fibers, which are considered to be early regenerating dystrophin negative fibers. Thus, laminin A appears in the muscle fiber basal lamina under certain conditions and, consequently, at least two heterotrimeric laminin variants are present in a pathological muscle. Two different laminin variants (M-B1-B2 and M-S-B2, where S is synapse-associated laminin) are expressed in neonatal and postsurgical rat liver (Wewer et al., Lab. Invest. 66:378–389 (1992), which is incorporated herein by reference).

FCMD patients exhibit developmental defects of the central nervous system including polymicrogyria and neuronal and glial heterotopias. Since extracellular matrix molecules have a role in mediating axon targeting in nervous system development (Hynes and Lander, *Cell* 68:303–322 (1992)), an abnormality in laminin M protein expression and localization can result in pleiotropic effects in the central nervous system of FCMD patients and in individuals with WWS or MEB.

Muscle tissue samples obtained from FCMD patients exhibited altered expression and localization of laminin M protein when visualized using the immunohistochemical method described herein. The altered expression and localization of laminin M protein were specific for FCMD patients and were not observed in patients suffering from Duchenne muscular dystrophy (DMD), other congenital muscular dystrophies unrelated to FCMD or other neuromuscular diseases.

In order to identify an effective therapeutic agent for treating an FCMD patient, a well characterized animal model of FCMD is desirable. Thus, another aspect of the present invention provides a mouse model of FCMD comprising the dy/dy mouse. Like FCMD in humans, dy/dy mice exhibit an autosomal recessive form of muscular dystrophy (Michelsen et al., *Proc. Natl. Acad. Sci., USA* 41:1079–1084 (1955)). Homozygous dy/dy mice have a more severe muscular dystrophy phenotype than the mdx mouse, which has been used as a model of Duchenne muscular dystrophy. However, dystrophin and the dystrophin related protein (DRP) are normal in dy/dy mice and the genetic defect that causes muscular dystrophy in dy/dy mice has not yet been described (Love et al., *Proc. Natl. Acad. Sci., USA* 88:3243–3247 (1991); Ohlendick et al., *Neuron* 7:499–508 (1991)).

The dy/dy mouse has been a useful model for developing new methods for identifying persons at risk of developing FCMD. The dy/dy phenotype in mice, like FCMD in humans, is characterized by decreased expression of laminin M protein. Immunofluorescence studies showed that the immunoreactivity of various anti-laminin M antibodies was decreased in the basement membrane of dy/dy mice (FIG. 8) and transmission electron microscopy studies demonstrated that the decrease in laminin M immunoreactive material is associated with basement membrane aberrations (FIG. 9). The absence of laminin M protein in muscle samples obtained from dy/dy mice was demonstrated by immunoblot analysis (FIG. 10), thus confirming that the appearance of muscular dystrophy in the dy/dy mouse is associated with the same changes observed in FCMD in humans. Furthermore, the dy/dy mouse model was used to demonstrate that the reduced expression of laminin M protein is associated with a decreased expression of mRNA encoding the M chain of laminin M (see Example VI and FIGS. 10 and 11).

As used herein, the term "expression" of laminin M protein refers to the presence of laminin M protein in a skeletal muscle sample. Expression of laminin M protein can be measured, for example, by using immunohistochemical methods to detect the presence of laminin M in a suitable tissue sample. "Altered" expression refers to the qualitative or quantitative determination that the amount of laminin M protein, for example, that is present in a tissue sample obtained from a subject is greater than or less than the amount of laminin M protein present in a control sample. The level of expression can be determined, for example, by detecting the intensity of labelling of a sample by a specific antibody, which is labelled with a detectable moiety.

The level of expression of M chain mRNA in a tissue sample also can be determined. As used herein, the "expression of M chain mRNA" refers to the presence in a sample of mRNA encoding the M chain of the laminin M protein. The "level of expression" of M chain mRNA can be determined using methods such as northern blot analysis or polymerase chain reaction (PCR) analysis, which are well known in the art and described in detail in Example VI, below (see, also, Sambrook et al., *Molecular Cloning: A laboratory manual* (Cold Spring Harbor Laboratory Press, 1989), which is incorporated herein by reference). The particular level of expression of M chain mRNA observed in a sample can be due to many factors such as the rate of transcription of the gene encoding the M chain of laminin M or the rate of degradation of the M chain mRNA in a cell.

As used herein, the term "sample" refers to a specimen obtained from a subject, which can be a human subject. In general, a tissue sample, which can be obtained, for example, by biopsy of muscle or placenta of an individual suspected of being predisposed to FCMD, is a suitable sample. In many cases, it is useful to prepare the sample as a tissue section, which can be examined by histologic analysis. Alternatively, proteins or nucleic acids can be extracted from a sample and can be examined using methods such as gel electrophoresis and appropriate "blotting" methods, which are well known in the art and described in detail below.

A sample can be obtained from a normal subject or from a test subject, who is suspected of being predisposed to FCMD and is being examined for altered expression or localization of laminin M protein or altered expression of M chain mRNA. As used herein, the term "suspected of being predisposed to FCMD" is used in its broadest sense to include any individual being tested for having the herein disclosed characteristics associated with FCMD.

A sample obtained from a normal subject can be used as a "control" sample, which is useful for comparison with a sample obtained from a test subject. A control sample can be, for example, a muscle sample or a placenta sample, which is obtained from an age- and sex-matched individual who does not exhibit and is not predisposed to a muscular dystrophy such as FCMD, WWS or MEB. A control sample exhibits a level of expression and a pattern of deposition of laminin M protein and a level of expression of M chain mRNA that is characteristic of the human population in general and does not significantly deviate from the normal levels of expression or pattern of localization expected for a person in the population. It is expected that, after a statistically significant number of control samples have been examined, an amount of laminin M expression per unit of a sample will be determined to be normal for a control sample. As used herein, a "normal" amount of laminin M protein in a control sample means an amount that is within an expected range for a person that is not predisposed to FCMD.

Altered expression of laminin M protein in a sample obtained from a test subject can be identified qualitatively by visually comparing, for example, photomicrographs of an immunohistochemically stained control sample with the sample obtained from the test subject. Alternatively, altered expression of laminin M protein can be measured quantitatively using, for example, densitometric analysis. Altered expression of laminin M protein also can be determined using methods of gel electrophoresis and, if desired, immunoblot analysis. Such methods are well known in the art and described in Example IV, below.

Altered localization of laminin M protein in a sample also can be determined. As used herein, the term "localization"

refers to the pattern of deposition of laminin M protein in a sample. The localization of laminin M protein also can be determined qualitatively or quantitatively. "Altered" localization refers to a pattern of laminin M protein deposition in a sample that is different from the pattern of localization observed in a control sample.

Qualitative and quantitative changes in the expression and localization of laminin M protein can be identified using standard histologic methods, such as the immunohistochemical methods described herein. Where immunohistochemical methods of analysis are used, an antibody specific for laminin M protein such as the 2G9 monoclonal antibody used in the studies described herein, can be obtained as described, for example, by Ehrig et al., *Proc. Natl. Acad. Sci. USA* 87:3264–3268 (1990) and Wewer et al., *J. Biol. Chem.* 258:12654–12660 (1983), each of which is incorporated herein by reference, and by Leivo and Engvall (1988). However, the 2G9 anti-laminin M antibody in not required to practice the invention and any other anti-laminin M antibody can be used provided its affinity for laminin M protein is at least about $10^6$ $mol^{-1}$ (Harlow and Lane, *Antibodies: A laboratory manual* (Cold Spring Harbor Laboratory Press, 1988), which is incorporated herein by reference; see page 28).

Routine methods can be used to raise anti-laminin M antibodies (see, for example, Wewer et al. (1983) and Harlow and Lane (1988), chapters 5–8). For example, laminin M protein (merosin) can be obtained from a commercial source (CalBiochem, San Diego, Calif.) and used as an immunogen to raise anti-laminin M antibodies. Antibodies useful for immunohistochemical identification of laminin M protein expression and localization can be monoclonal antibodies, such as the 4F11 and 2G9 monoclonal antibodies, or polyclonal antibodies, which can be obtained using the method described by Leivo and Engvall (1988). In addition, anti-laminin M monoclonal antibodies are available from commercial sources such as Chemicon, Inc. (California). The usefulness of an anti-laminin M antibody in the diagnostic assays described herein can be readily determined using routine immunologic and immunohistochemical methods as described, for example, by Harlow and Lane (1988).

An anti-laminin M antibody can be labeled using methods well known in the art (see, for example, Harlow and Lane, 1988; chap. 9). For example, an antibody can be labelled with various detectable moieties including a radionuclide, such as iodine-125, an enzyme, biotin or a fluorochrome. Following contact of a labelled antibody with a sample such as a tissue section, as described in detail, below, specifically bound labelled antibody can be identified by detecting the particular moiety. A sample that is contacted, for example, with a labelled antibody and that thereafter contains specifically bound labelled antibody is referred to herein as a "labelled sample."

Alternatively, a labelled second antibody can be used to identify specific binding of an unlabelled first antibody such as an anti-laminin M antibody. A second antibody is specific for the particular class of the first antibody. For example, if an anti-laminin M antibody is of the IgG class, a second antibody will be an anti-IgG antibody. Such second antibodies are readily available from commercial sources (Biorad, California). The second antibody can be labelled with any of the detectable moieties described above, including a fluorochrome such as fluorescein isothiocyanate, as described below. When a sample is labelled using a second antibody, the sample is first contacted with a first antibody, then the sample is contacted with the labelled second antibody, which specifically binds to the first antibody and results in a labelled sample.

Qualitative analysis of the intensity and localization of specifically bound antibody in a labelled sample can be determined by various methods. For example, where a detectable moiety is a radionuclide, an appropriate film emulsion can be exposed to the labelled sample and, following development of the exposed emulsion, the relative number of "grains" in various samples can be determined by visual inspection. Alternatively, photomicrographs can be obtained of a fluorescently or colorimetrically labelled sample and the photomicrographs can be visually inspected to determine the relative intensity of labelling. It can be useful to further relate the intensity of labelling with the pattern of labelling. For example, patterns of labelling may be distinguished as normal, faint or blurred, intense, partially deficient and negative, as described below.

Quantitative changes in the expression and localization of laminin M protein also can be determined. Various methods are useful for quantitating the expression and localization of laminin M protein, depending on the detectable moiety used to label, for example, an antilaminin M antibody. Thus, where a detectable moiety is radioactive, the amount of specific antibody binding can be quantitated using scintillation spectrometry. In some cases, however, preparation of a labelled sample for scintillation spectrometry requires destruction of the native structure of the sample, thus precluding a determination of the localization of the specific label. Thus, where it is desirable to maintain the structure of the sample, a radiolabelled sample can be used to expose a film emulsion, which, following development, can be subjected to densitometric analysis. Alternatively, a detectable moiety such as a fluorochrome can be used and specific binding can be quantitated using densitometric methods. Methods of densitometric analysis of fluorescently labelled samples are well known in the art and described in detail below.

Although anti-laminin M antibodies are useful for determining the expression and localization of laminin M protein in a sample, any molecule that binds to laminin M protein can be used, provided the molecule binds to laminin M protein with relatively high specificity. Heparin is an example of a molecule that can bind to laminin and, therefore, can be used to determine the expression and localization of laminin M protein in a sample (see Engvall et al., *Exptl. Cell Res.* 198:115–123 (1992), which is incorporated herein by reference).

The level of expression of M chain mRNA in a cell also can be determined and can be used to identify an individual that is predisposed to FCMD. Methods for determining the level of expression of M chain mRNA in a sample are well known in the art and include, for example, northern blot analysis, which can be used to determine whether M chain mRNA is expressed at a normal level in a test sample. Northern blot analysis also can be used to determine whether the M chain mRNA that is expressed in a cell is a full length transcript. For example, an RNA sample obtained from a tissue sample can be contacted with a nucleic acid probe that hybridizes to the mRNA encoding the M chain of laminin M. One skilled in the art would know that the probe can be a DNA or RNA probe and can be prepared from a cDNA encoding the M chain or can be synthesized as an oligonucleotide. In addition, the skilled artisan would recognize that such hybridization should be performed under stringent conditions, which can be determined empirically (see, for example, Sambrook et al., *Molecular Cloning: A laboratory manual* (Cold Spring Harbor Laboratory Press 1989), which is incorporated herein by reference). The size of a full length transcript can be readily determined as shown, for example, in FIG. 11, below, which indicates the full length mouse M chain transcript is approximately 10 kilobases (kb). Methods for isolating intact total RNA and poly A+ mRNA and for performing northern blot analysis are described below and are well known in the art (Sambrook et al., 1989).

A sensitive method of determining the level of expression of M chain mRNA in a sample is the reverse transcriptase-polymerase chain reaction (RT-PCR), which is described below and well known in the art (see, for example, H. A. Erlich, *PCR Technology: Principles and applications for DNA amplification* (Stockton Press, 1989), which is incorporated herein by reference; see chap. 8). The RT-PCR method is particularly useful for examining a sample that fails to give a detectable signal by northern blot analysis. Due to the amplification steps involved in PCR analysis, a rare M chain mRNA can be identified in a sample. The identification of a rare M chain mRNA in a sample can be useful, for example, in distinguishing potential molecular mechanisms for the cause of FCMD. For example, the complete absence of M chain mRNA can indicate that a defect in the gene encoding M chain mRNA prevents transcription of the gene. Alternatively, the presence of a low level of M chain mRNA can indicate that the mRNA is unusually susceptible to degradation in the cell or is transcribed at an abnormally low rate. Knowledge of such potential different mechanisms leading to the FCMD phenotype can allow intervention at the appropriate molecular level.

The availability of the above-described methods for identifying an individual predisposed to a muscular dystrophy such as FCMD, which is characterized by altered expression and localization of laminin M protein and altered expression of M chain mRNA, allows for the development of diagnostic assays useful for identifying such individuals. As used herein, the term "diagnostic assay" refers to the specific use of the methods described herein to identify an individual predisposed to a muscular dystrophy such as FCMD. Such diagnostic assays are particularly useful as prenatal diagnostic assays, which can be used to determine whether a fetus is predisposed to FCMD. For prenatal diagnosis, for example, a sample can be obtained by biopsy of muscle tissue from the fetus or by biopsy of placenta from the pregnant mother.

The materials for performing the diagnostic assays of the present invention can be made available in a kit and sold, for example, to hospitals, clinics and doctors. A kit for detecting altered expression and localization of laminin M protein, for example, can contain a reagent such as an anti-laminin M antibody and, if desired, a labelled second antibody, a suitable solution such as a buffer for performing, for example, an immunohistochemical reaction and a known control sample for comparison to the test sample.

A kit for detecting altered M chain mRNA expression in a sample obtained from an individual suspected of being predisposed to a FCMD also can be prepared. Such a kit can contain, for example, a reagent such as an oligonucleotide probe that hybridizes to M chain mRNA, suitable solutions for extracting mRNA from a tissue sample or for performing the hybridization reaction and a control mRNA sample for comparison to the test sample or a series of control mRNA samples useful, for example, for constructing a standard curve.

Such diagnostic assay kits are particularly useful because the kits can contain a predetermined amount of a reagent that can be contacted with a test sample under standardized conditions to obtain an optimal level of specific binding of the reagent to the sample. The availability of standardized methods for identifying an individual predisposed to a muscular dystrophy such as FCMD will allow for greater accuracy and precision of the diagnostic methods.

The advantage of being able to identify individuals predisposed to exhibiting the clinical symptoms of FCMD can be greatly enhanced by identifying effective therapeutic agents for reducing or preventing the clinical symptoms of FCMD. The dy/dy mouse provides a particularly useful system for screening potential therapeutic agents such as drugs, which can reduce or prevent the clinical symptoms associated with FCMD. As used herein, the term "clinical symptom" is used in its broadest sense to mean any objective or subjective indicia normally associated with a muscular dystrophy. Thus, the definition of the term "clinical symptoms" includes the common clinical meanings of the terms "sign" and "symptom." Clinical symptoms associated with muscular dystrophy include, for example, myofiber hypertrophy, muscle tissue fibrosis and sclerosis, muscle atrophy and rapid onset of muscle fatigue.

In general, the severe tissue damage observed in a patient having a muscular dystrophy such as DMD is not due to the primary defect, i.e., the abnormal production of dystrophin but, instead, results from the mechanical stress-induced tissue damage that occurs when the patient uses the dystrophic muscle. As used herein, the term "mechanical stress-induced tissue damage" refers to the tissue damage caused by using a muscle that expresses a defective laminin M protein. This muscle tissue damage induces an inflammatory-type, wound healing response, which ultimately causes the more severe clinical symptoms such as muscle tissue sclerosis that are associated with muscular dystrophy (Clarke et al., *J. Cell Sci.* 106:121–133 (1993); Border et al., *J. Clin. Invest.* 90:1–7 (1992), each of which is incorporated herein by reference).

As disclosed herein, a defect associated with FCMD is the decreased in the level of expression and an altered pattern of localization of laminin M protein in skeletal muscle. However, as in DMD, it is the physiologic response to mechanical stress-induced muscle tissue damage that leads to the severe clinical symptoms observed in FCMD patients. It is well recognized that the expression of various growth factors or cytokines such as transforming growth factor-β (TGFβ), tumor necrosis factor (TNF), interleukin-1 (IL-1) and basic fibroblast growth factor (bFGF) in an area of inflammation contribute to the fibrosis and sclerosis associated with various chronic inflammatory diseases (see, for example, Border et al. (1992); and Okuda et al., *J. Clin. Invest.* 86:453–462 (1990); Czaja et al., *J. Cell Biol.* 108:2477–2482 (1989), each of which is incorporated herein by reference). Thus, the identification of agents such as drugs or antibodies that reduce or prevent expression of such growth factors or cytokines and, in turn, can be used to reduce or prevent clinical symptoms in FCMD patients. However, in an effort to minimize the severity of the mechanical stress-induced tissue damage in DMD patients, anti-inflammatory agents such as corticosteroids were administered but were relatively ineffective in reducing the clinical symptoms of DMD.

The dy/dy mouse model can be used as a screening assay to identify effective agents that can reduce or prevent clinical symptoms such as muscle tissue sclerosis that are associated with a muscular dystrophy such as FCMD. Such therapeutic agents can be administered to an FCMD patient and can result in a profound improvement in the quality of life of FCMD patients. As used herein, the term "agent" refers to a chemical or biological molecule that is potentially useful for reducing or preventing the clinical symptoms associated with FCMD. Such an agent, which also is referred to as a "potentially effective agent," can be a drug, a peptide, a protein such as an antibody or a nucleic acid.

An "effective agent" or an "effective therapeutic agent" is an agent that can reduce or prevent the clinical symptoms associated with FCMD. An example of an effective agent can be an anti-TGFβ antibody, which can prevent TGFβ activity in a cell and, as a result, can reduce or prevent muscle tissue sclerosis in an FCMD patient. Other proteins such as decorin also are known to bind TGFβ and, therefore, can be used to reduce or prevent the activity of TGFβ in an FCMD patient (Yamaguchi et al., *Nature* 346:281-284 (1990), which is incorporated herein by reference). In addition, members of the steroid hormone superfamily can regulate the expression of TGFβ (see, for example, Wakefield et al., *J. Cell Sci. Suppl.* 13:139-148 (1990), which is incorporated herein by reference).

An effective agent also can be a drug or a peptide, for example, that can bind a specific growth factor or growth factor receptor and prevent the activity of the growth factor in vivo. Peptides are particularly useful for inhibiting the activity of a growth factor such as bFGF or a cytokine involved in an inflammatory reaction that leads to the severe, chronic clinical symptoms of FCMD (see, for example, Yayon et al., *Proc. Natl. Acad. Sci., USA* 90:10643-10647 (1993), which is incorporated herein by reference). For example, peptides can be synthesized in large amounts and easily administered to a patient. In addition, peptides that are useful as effective agents can be identified by screening a "phage epitope library" as described, for example, by Yayon et al. (1993), and by Balass et al., *Proc. Natl. Acad. Sci. USA* 90:10638-10642 (1993), which is incorporated herein by reference. Chemical agents such as drugs also can reduce or prevent the activity of a growth factor.

An agent can be an effective therapeutic agent by reducing or preventing the clinical symptoms of FCMD that are due to events such as the inflammatory-type response that occurs in these patients. However, an effective therapeutic agent also can act at the level of the laminin M protein defect associated with FCMD. Such an effective agent can be, for example, a nucleic acid molecule that encodes a non-defective laminin M protein. Such a nucleic acid can be introduced into muscle cells of FCMD patients and can be induced to express laminin M in a cell. In addition, an antisense nucleic acid or a ribozyme specific for an mRNA encoding the M chain of laminin M can be used to decrease the level of defective laminin M that is produced in a muscle cell. Such an antisense nucleic acid or a ribozyme is particularly useful if it is designed only to hybridize to a nucleic acid encoding a defective laminin M protein but not to a nucleic acid encoding a normal laminin M protein. Methods for constructing vectors expressing antisense nucleic acids or ribozymes are well known in the art and described, for example, by Altman, *Proc. Natl. Acad. Sci., USA* 90:10898-10900 (1993), and the references cited therein, each of which is incorporated herein by reference.

Methods for introducing nucleic acid molecules into a cell are well known. A particularly useful method for introducing a nucleic acid molecule into a cell is to incorporate the nucleic acid into a vector such as a viral vector. Viral vectors that are compatible with a targeted cell are particularly useful for introducing a nucleic acid encoding laminin M into a cell. For example, recombinant adenoviruses having general or tissue-specific promoters can be used to deliver laminin M expression constructs into a variety of types of tissues and cells, including non-mitotic muscle or nerve cells. Recombinant adeno-associated viruses also are useful and have the added advantage that the recombinant virus can stably integrate into the chromatin of even quiescent non-proliferating cells such as neurons of the central and peripheral nervous systems (Lebkowski et al., *Mol. Cell. Biol.* 8:3988-3996 (1988), which is incorporated herein by reference).

Specific vectors also can be constructed to express specific receptors or ligands, which can modify or alter target specificity through receptor mediated events. Such vectors can be constructed using recombinant DNA techniques or synthetic chemistry procedures. In addition, a viral vector can be made tissue-specific by incorporating a tissue-specific promoter or enhancer such as the muscle creatine kinase enhancer into the vector, in order to direct expression of a nucleic acid encoding laminin M to muscle cells (Dai et al., *Proc. Natl. Acad. Sci. USA* 89:10892-10895 (1992); Cox et al., *Nature* 364:725-729 (1993), each of which is incorporated herein by reference).

Retroviral vectors are particularly useful for in vivo targeting and therapy procedures (Anderson, *Science* 256:808-813 (1992), which is incorporated herein by reference). Retroviral vectors can be constructed either to function as infectious particles or to undergo only a single initial round of infection. In the former case, the genome of the virus is modified so that it maintains the necessary genes, regulatory sequences and packaging signals to synthesize new viral proteins and RNA. However, genes conferring oncogenic potential of these viruses is destroyed. After the viral proteins are synthesized, the host cell packages the RNA into new viral particles, which can undergo further rounds of infection. The viral genome also is engineered to encode and express the desired recombinant gene.

In the case of non-infectious viral vectors, the helper virus genome can be mutated to destroy the viral packaging signal required to encapsulate the RNA into viral particles. However, the helper virus retains structural genes required to package a co-introduced recombinant virus containing a gene of interest. Without a packaging signal, viral particles will not contain a genome and, thus, cannot proceed through subsequent rounds of infection. Examples of such retroviral vectors include SAX, N2 and SVXβ(RO) (Eglitis and Anderson, *BioTechniques* 6:608-614 (1988), which is incorporated herein by reference). Methods for constructing and using these and other viral vectors are well known in the art and reviewed, for example, in Miller and Rosman, *BioTechniques* 7:980-990 (1992), which is incorporated herein by reference. Retrovirus vectors are particularly useful when the vector contains a muscle tissue-specific gene regulatory element such as the muscle creatine kinase enhancer described above.

Other methods for introducing a nucleic acid encoding laminin M into a cell also are known. For example, yeast artificial chromosomes can be used to introduce a large gene sequence such as the laminin M gene into a cell (Peterson et al., *Proc. Natl. Acad. Sci., USA* 90:11207-11211 (1993), which is incorporated herein by reference). Furthermore, an effective agent can be a nucleic acid that increases the level of a protein other than laminin M. For example, laminin A protein levels can increase in a muscle cell that expresses defective laminin M, perhaps as a compensatory response by the muscle cell due to the lack of normal laminin M protein. Thus, introduction of a nucleic acid encoding laminin A into a muscle cell of an FCMD patient can alleviate the clinical symptoms due to the primary laminin M protein defect in FCMD patients. However, laminin A protein levels in a cell also can be increased by contacting a muscle cell with an agent such as retinoic acid, which may increase the expression of the laminin A gene. For example, treatment of an FCMD patient with retinoic acid can result in increased laminin A gene expression and, as a result, can alleviate the clinical symptoms due to the primary laminin M defect in the patient.

The dy/dy mouse model can be used to examine the effectiveness of various agents by administering to the mouse a pharmacological composition comprising a potentially effective agent and a pharmaceutically acceptable carrier. Pharmaceutically acceptable carriers are well known in the art and include aqueous solutions such as physiologically buffered saline or other solvents or vehicles such as glycols or glycerol. The particular pharmaceutically acceptable carrier to be used would depend, for example, on the route by which the pharmaceutical composition is to be administered, which, in turn, is determined by whether treatment is to be localized or systemic. For example, if the effectiveness of an agent in treating a developing fetus in utero is to be examined, a pharmaceutically acceptable carrier can be selected based on its ability to facilitate transport of the agent across the placenta.

Since the muscular dystrophy in dy/dy mice, which, like FCMD in humans, is an autosomal recessive genetic disease, this mouse model provides a system that produces a predictable percentage of offspring exhibiting the muscular dystrophy phenotype. Thus, the dy/dy mouse model provides the additional advantage of allowing for the screening of an agent that can be used for in utero treatment of an individual predisposed to a muscular dystrophy characterized by reduced expression of laminin M. The identification of such effective therapeutic agents can allow for early intervention in the disease process. However, since the inflammatory-type response only occurs due to mechanical stress-induced tissue damage, which does not occur until after birth when the muscle is used, an effective agent for administration in utero would likely be limited to an agent such as a nucleic acid encoding a non-defective laminin M protein that can correct the primary laminin M protein defect.

The method of administering a pharmaceutically acceptable composition comprising an agent will depend, for example, on the particular agent. Preferably, the composition can be administered orally and, therefore, provide a systemic distribution without requiring, for example, an injection. A composition also can be administered by injection, for example, intramuscularly, subcutaneously or intravenously. In addition, an agent can be administered using, for example, a subcutaneous pump or a patch, which allows prolonged, measured administration of the agent.

An effective therapeutic agent can be readily identified using the methods described herein or otherwise known in the field. For example, following administration of an agent to a dy/dy mouse, the level of expression of laminin M protein or M chain mRNA can be determined. An effective agent can be identified by its ability to increase the level of expression of laminin M protein or mRNA. In addition, an effective agent can be identified by its ability to decrease the levels of growth factors or cytokines in a muscle tissue sample and, therefore, reduce or prevent the inflammatory-type response due to mechanical stress-induced tissue damage.

As an initial screening method, an effective therapeutic agent can be identified by monitoring, for example, the physical capacity of a treated dy/dy mouse using a treadmill test (Clarke et al., 1993). It is well known that a muscular dystrophy patient can appear normal. However, the effects of muscular dystrophy can be observed by physically challenging a patient. Such a challenged patient is characterized by being easily fatigued. Similarly, dy/dy mice can be examined for the onset of fatigue using, for example, a treadmill test. A potentially effective agent can be administered to a dy/dy mouse and the onset of fatigue in the treated mouse as compared to an untreated control mouse can be compared. An effective agent can be identified by increasing the stamina of a treated mouse in such a test.

The effectiveness of an agent can be further characterized by histologically examining a treated mouse following a physical challenge such a performance on a treadmill. Tissue samples can be obtained from a treated mouse and from a control mouse and can be examined, for example, for morphological evidence of tissue damage or for expression of growth factors or cytokines such as TGFβ and bFGF. An effective agent can be identified, for example, by its ability to reduce or prevent the expression of factors involved in mediating an inflammatory-type wound healing response.

The following examples are intended to illustrate but not limit the present invention.

EXAMPLE I

METHODS FOR IMMUNOHISTOCHEMICAL ANALYSIS OF HUMAN TISSUE SAMPLES

This example discloses methods for performing an immunohistochemical determination of the expression and localization of cytoskeleton/basal lamina proteins in tissue samples. The results obtained using muscle samples and placenta are described in Examples II and III, below.

Clinical material:

Limb-muscle specimens were obtained with informed consent from the biceps bracii or rectus femoris of normal subjects or from patients having FCMD (17 cases), other congenital muscular dystrophy unrelated to FCMD (CMD; 13 cases), Duchenne muscular dystrophy (DMD; 16 cases) or other neuromuscular diseases (OND; 18 cases). OND patients include those with spinal muscular atrophy, menaline myopathy, myotubular myopathy, mitochondrial myopathy, inflammatory myopathies or non-specific muscle weakness or high creatine kinasemia. Clinical profiles of the various patients are provided in Table 1. Placenta tissue was obtained from a 9 week old fetus following clinical abortion. Muscle and placenta tissue samples were flash frozen in isopentane chilled using liquid nitrogen.

Antibodies:

The antibodies used in this study are listed in Table 2. The specificity of four different anti-human laminin subunit monoclonal antibodies, 11D5, 4E10, 2E8 and 2G9, has been described by Ehrig et al. (1990). Monoclonal or polyclonal anti-human laminin A chain, B1 chain, merosin (laminin M) and EHS sarcoma antibodies also were used (Chemicon Inc.). Polyclonal rabbit anti-human type IV collagen antiserum was purchased from Advance Inc. (Tokyo). Rabbit anti-human erythrocyte spectrin antiserum was obtained from Transformation Res. Inc. (MA).

Monoclonal anti-dystrophin antibodies were raised against synthetic peptides corresponding to amino acids 440 to 489 of the rod domain and amino acids 3498 to 3544 of the carboxy terminus of human fetal skeletal muscle dystrophin as described by Arahata et al., *Proc. Nat'l. Acad. Sci., USA* 86:7154–7158 (1989) and by Arahata et al., *J. Neurol. Sci.* 101:148–156 (1991), each of which is incorporated herein by reference. Polyclonal 6–10 anti-dystrophin antiserum was prepared as described by Lidov et al., *Nature* 348:725–728 (1990) and by Byers et al. *J. Cell. Biol.* 115:411–421 (1991), each of which is incorporated herein by reference. Affinity-purified fluorescein isothiocyanate (FITC)-labeled goat F(ab')2 anti-mouse and anti-rabbit IgG were obtained from Biorad and used as second antibodies.

TABLE 1

Clinical profiles of patients

| Clinical[a] diagnosis | Number of patients | Sex M | Sex F | Age Range | Age Mean | CK(U/l)[b] Range | CK(U/l)[b] Mean |
|---|---|---|---|---|---|---|---|
| FCMD | 17 | 12 | 5 | 4M–6Y | 1Y9M | 763–10130 | 3618 |
| Other CMD | 13 | 6 | 7 | 5M–12Y | 2Y1M | 176–3786 | 1271 |
| DMD | 16 | 16 | 0 | 1Y–12Y | 4Y | 6480–64855 | 10508 |
| OND | 18 | 8 | 10 | 5M–39Y | 8Y9M | 18–15980 | 3064 |

[a]FCMD: Fukuyama congenital muscular dystrophy
Other CMD: congenital muscular dystrophy unrelated to FCMD
DMD: Duchenne muscula dystrophy
OND: other neuromuscular diseases include nemaiine myopathy(3), myotubular myopathy(1), mitochondrial myopathy(3), motor neuron disase(1), polymyositis(1), dermatomyositis(1), McArdle disease(1), congenital fiber type disproportion(1), neuropathic changes(3) and nonspecific myopathy(3).
[b]CK: creatine kinase (normal range: 12–75 U/l)

Immunocytochemistry:

Tissue samples were immunoreacted with a series of antibodies as listed in Table 2. Serial sections (6µ) were obtained using a cryostat and thawed on gelatinized cover slips. Tissue sections were fixed in 100% ice-cold acetone for 5 min, air dried for 30 min, soaked in 0.1% nonidet-P40 for 3 min, then preincubated with PBS containing 2% BSA and 5% heat-inactivated normal goat serum, pH 7.4. Sections were sequentially incubated with each antibody for 2 hr at 37° C., then incubated with the second antibody (10 ug/ml) for 1 hr at room temperature. Sections were mounted using a glycerol-based medium and examined using a Zeiss Axiophoto microscope with epifluorescence. Specificity of immunostaining was examined by replacing the primary antibody with a control mouse myeloma IgG.

Classification of immunocytochemical staining patterns and quantitation of muscle fibers according to the staining patterns:

Each cover slip contained 5 to 7 frozen sections from different patient biopsies and one biopsy obtained from a known normal control muscle. Fluorescent photographs were taken by exposing either Polaroid type 57 high speed 4×5 film or Fujichrome 400 film (Fuji) for 60 seconds. Staining patterns of each immunoreacted muscle fiber for laminin subunits (A, B1, B2 and M), type IV collagen, dystrophin and spectrin were classified as described by Arikawa et al. (1991), which is incorporated herein by reference, with slight modification into 5 patterns: 1) normal, 2) faint or blurred (an obscure stain of basal lamina lacking clear outline), 3) intense, 4) partially deficient or 5) negative. For quantitative analysis of the immunostaining pattern, 450 to 840 randomly

TABLE 2

Antibodies used in this study

| Antigen | Antibody designation | Antibody type | Immunogen source |
|---|---|---|---|
| Laminin A | 11D5,A | Mouse mAb | Human |
| Laminin B1 | 4E10,B1 | Mouse mAb | Human |
| Laminin B2 | 2E8 | Mouse mAb | Human |
| Laminin M | 2G9, merosin | Mouse mAb | Human |
| Laminin |  |  |  |
| (EHS tumor) | EHS | Rabbit serum | Human |
| Collagen IV |  | Rabbit serum | Human |
| Dystrophin | 2-5E2 | Mouse mAb | * |
|  | 4-4C5 | Mouse mAb | * |
|  | 6-10 | Rabbit serum | ** |
| Spectrin |  | Rabbit serum | Human |

*Monoclonal antibodies (mAbs) which were raised against synthetic peptides corresponding to amino acid 440–489 (2-5E2) and 3495-3544 (4-4C5) of human fetal skeletal muscle dystrophin.
**polyclonal antibody which was kindly provided by Drs. Louis M. Kunkel and Timothy J. Byers.

selected muscle fibers from each specimen were analyzed on the photograph and the number of immunoreacted fibers for each antibody was counted for each of the 5 different patterns (Table 3).

Quantitative densitometric analysis of immunostaining intensity:

Measurement of the immunolabelling intensity of fluorescence at the sarcolemma was calculated using an IBAS Rel. 2.0 automatic image analyzer (Carl Zeiss Vision Co. Ltd.) with appropriate control. 3264 pixels of a randomly chosen rectangular region (56006.25 µm$^2$) in each muscle specimen were measured (Table 4.a.). Positive immunostaining of laminin A, laminin B1, laminin B2 and type IV collagen in vascular basal lamina was erased from the screen prior to beginning the analysis and the mean cytoplasmic grey level was subtracted before calculating the immunostaining intensity. Histograms showing the gray value for all pixels in an image were displayed with the statistical evaluation (see FIG. 3). Total plasma membrane length of a region was determined to allow calculation of the immunolabelling intensity per unit membrane length (Table 4.b.). The results of these studies are described in Example II.

EXAMPLE II

IMMUNOHISTOCHEMICAL ANALYSIS OF HUMAN SKELETAL MUSCLE SAMPLES

Figures 4A, 4B, 4C:
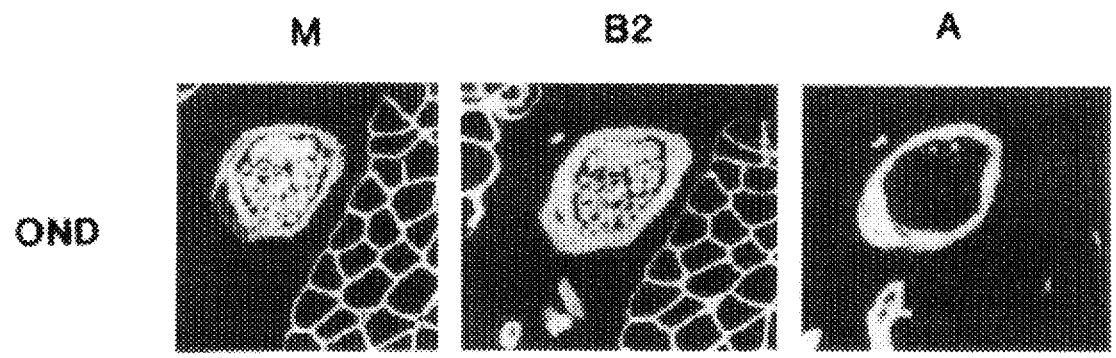
FIGS. 4.a. to 4.i. Indirect immunofluorescence staining of consecutive frozen muscle sections of control OND (FIGS. 4a–4c) and two FCMD patients (FIGS. 4d–4f and FIGS. 4g–4i). Immunostaining of laminin M in FCMD muscle is less intense (FIG. 4d), as compared to control OND, or is undetectable (FIG. 4g). Endoneurial basal lamina of intramuscular nerve of OND stains intensely for laminin M, laminin B1 (not shown) and laminin B2 but does not stain for laminin A. Magnification ×300.
Figures 4D, 4E, 4F:
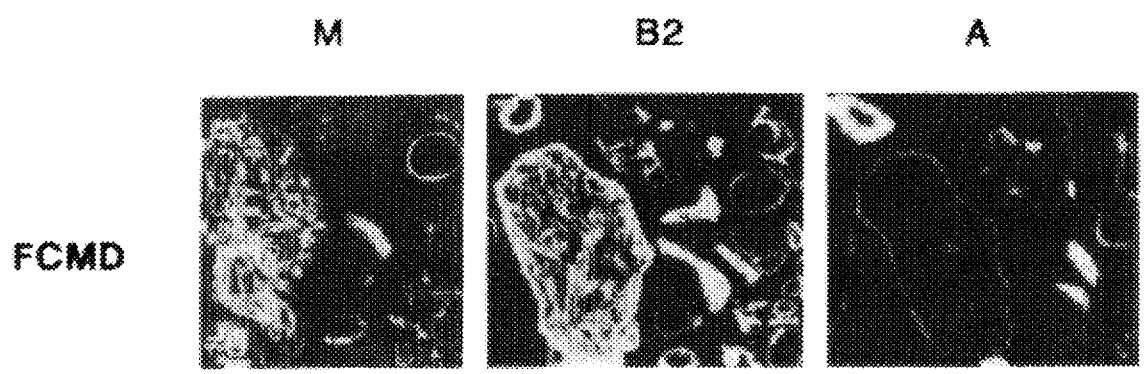

Laminin:

In control OND and other CMD muscle samples, laminin M (merosin), laminin B1 and laminin B2, each showed a sharply delineated ring of immunostaining (FIG. 1a, 1b and 1c, respectively, and FIG. 4a). Endoneurial basement membrane of intramuscular nerves also

TABLE 3

Comparison of immunocytochemical staining patterns

| | Total of normal fibers (%) | Total of abnormal fibers (%) | Detail of abnormal fibers (%) | | | |
|---|---|---|---|---|---|---|
| | | | Faint/Blur | Intense | Partial | Negative |
| Laminin H | | | | | | |
| FCMD | 3.1 ± 4.2 | 96.9 ± 4.2* | 74.0 ± 29.4* | 0.0 | 8.1 ± 4.8# | 14.3 ± 3.4 |
| Other CMD | 94.9 ± 2.3 | 5.1 ± 4.2 | 3.0 ± 1.9 | 1.6 ± 1.5 | 0.5 ± 0.7 | 0.0 |
| DMD | 92.5 ± 4.0 | 7.5 ± 4.0** | 5.8 ± 2.9** | 0.6 ± 0.5 | 0.9 ± 1.5## | 0.0 |
| OND | 98.7 ± 1.7 | 1.3 ± 1.7 | 1.3 ± 1.7 | 0.0 | 0.0 | 0.0 |
| Laminin B1 | | | | | | |
| FCMD | 3.9 ± 4.0 | 96.1 ± 4.0* | 74.0 ± 31.3* | 0.0 | 8.1 ± 4.8# | 14.0 ± 28.9 |
| Other CMD | 94.2 ± 4.1 | 5.8 ± 4.1 | 3.7 ± 3.2 | 1.7 ± 1.8 | 0.4 ± 0.2 | 0.0 |
| DMD | 92.8 ± 5.1 | 7.2 ± 5.1** | 5.0 ± 3.2** | 1.3 ± 1.6 | 0.8 ± 1.0## | 0.2 ± 0.4 |
| OND | 97.5 ± 2.1 | 2.6 ± 2.1 | 0.1 ± 1.9 | 0.0 | 0.4 ± 0.2 | 0.0 |
| Laminin B2 | | | | | | |
| FCMD | 14.3 ± 3.4 | 85.7 ± 3.4* | 76.8 ± 4.8* | 1.6 ± 1.3 | 6.2 ± 1.6* | 1.1 ± 0.6 |
| Other CMD | 97.1 ± 2.0 | 2.9 ± 2.0 | 1.4 ± 1.2 | 0.9 ± 1.2 | 0.4 ± 0.4 | 0.0 |
| DMD | 93.3 ± 4.5 | 6.7 ± 4.5** | 4.1 ± 2.6** | 1.7 ± 2.0 | 0.9 ± 0.9** | 0.0 |
| OND | 97.8 ± 2.0 | 2.2 ± 2.0 | 1.9 ± 2.2 | 0.2 ± 0.2 | 0.2 ± 0.3 | 0.0 |
| Collagen IV | | | | | | |
| FCMD | 16.9 ± 6.7 | 83.1 ± 6.7* | 69.6 ± 10.1* | 1.4 ± 1.1 | 11.3 ± 5.6* | 0.9 ± 0.8 |
| Other CMD | 88.2 ± 3.8 | 11.8 ± 3.8 | 6.8 ± 3.0 | 1.9 ± 1.0 | 3.0 ± 1.5 | 0.0 |
| DMD | 87.7 ± 5.3 | 12.3 ± 5.3** | 9.5 ± 2.7** | 1.6 ± 0.8 | 1.4 ± 1.2** | 0.0 |
| OND | 97.7 ± 2.8 | 2.3 ± 2.8 | 1.8 ± 2.3 | 0.3 ± 0.4 | 0.1 ± 0.2 | 0.0 |
| Dystrophin | | | | | | |
| FCMD | 74.2 ± 6.2 | 26.8 ± 6.2* | 3.4 ± 1.3! | 3.1 ± 2.1# | 13.9 ± 5.3* | 6.7 ± 3.0* |
| Other CMD | 96.7 ± 2.1 | 3.3 ± 2.1** | 1.5 ± 1.5!! | 0.2 ± 0.1## | 1.1 ± 0.6 | 0.5 ± 0.5** |
| DMD | 0.0 | 100.0 | 0.0 | 0.0 | 0.0 | 100.0 |
| OND | 97.8 ± 3.5 | 2.2 ± 3.5 | 0.7 ± 1.0 | 0.1 ± 0.1 | 1.1 ± 3.0** | 0.2 ± 0.5 |
| Spectrin | | | | | | |
| FCMD | 79.8 ± 8.2 | 20.2 ± 8.2* | 5.9 ± 2.9 | 3.3 ± 6.4 | 4.8 ± 1.3* | 2.3 ± 2.8 |
| Other CMD | 94.0 ± 3.2 | 6.0 ± 3.2 | 2.7 ± 1.4 | 3.0 ± 2.3 | 0.2 ± 0.2 | 0.0 |
| DMD | 93.9 ± 2.2 | 6.1 ± 2.2** | 3.5 ± 0.1 | 1.5 ± 1.5 | 0.6 ± 0.5** | 0.5 ± 0.3 |
| OND | 98.5 ± 2.1 | 1.5 ± 2.1 | 0.1 ± 1.3 | 0.3 ± 0.7 | 0.2 ± 0.2 | 0.0 |

Each of 5 age-matched patients was examined.
FCMD: Fukuyama congenital muscular dystrophy;
Other CMD: non-FCMD
DMD: Duchenne muscular dystrophy;
OND: Other neuromuscular diseases
A total of 450–880 fibers from each specimen was analyzed.
Values are the mean ± SD and show the significant difference by Student's t-test between * and ** ($P < 0.005$).
# and ## ($P < 0.01$).
! and !! ($P < 0.05$).

TABLE 4

Mean immunolabelling intensity in a rectangular region (56,006 um$^2$)
(analyzed with IBAS system)

| | Laminin M | Laminin B1 | Laminin B2 | Collagen IV | Dystrophin | Spectrin |
|---|---|---|---|---|---|---|
| FCMD | 16.2 ± 11.3* | 20.8 ± 7.5* | 23.7 ± 9.9* | 44.2 ± 10.5 | 29.8 ± 12.0* | 43.8 ± 9.6 |
| Other CMD | 54.3 ± 20.3 | 48.2 ± 11.8 | 48.0 ± 9.4** | 37.3 ± 6.5 | 31.6 ± 7.3 | 38.3 ± 10.4 |
| DMD | 47.2 ± 6.9** | 43.3 ± 10.6** | 48.5 ± 4.8 | 45.4 ± 15.8 | 5.0 ± 2.1** | 52.6 ± 17.2 |
| OND | 72.8 ± 17.5 | 59.0 ± 26.9 | 54.9 ± 18.5 | 41.9 ± 19.2 | 31.0 ± 5.2 | 59.0 ± 26.9 |

Mean immunolabelling intensity per unit plasma membrane
(analyzed with IBAS system)

| | Laminin M | Laminin B1 | Laminin B2 | Collagen IV | Dystrophin | Spectrin |
|---|---|---|---|---|---|---|
| FCMD | 16.3 ± 10.1# | 21.2 ± 5.2° | 26.4 ± 9.3° | 49.7 ± 8.0 | 32.4 ± 6.9 | 50.1 ± 12.4 |
| Other CMD | 49.5 ± 20.5## | 44.1 ± 17.1°° | 45.1 ± 15.3°° | 35.7 ± 14.2 | 29.9 ± 12.0 | 36.3 ± 16.1 |

TABLE 4-continued

| | | | | | | |
|---|---|---|---|---|---|---|
| DMD | 50.8 ± 6.5 | 46.7 ± 10.0 | 48.8 ± 9.6 | 48.8 ± 15.3 | 4.0 ± 1.8* | 56.9 ± 19.6 |
| OND | 63.3 ± 15.4 | 51.6 ± 25.0 | 36.3 ± 13.5 | 36.2 ± 15.8 | 27.1 ± 5.3** | 45.9 ± 7.9 |

Each of 5 age-matched patients was examined.
Values are the mean ± SD and show the significant difference by Student's t-test between * and ** (P < 0.005),
# and ## (P < 0.01),
° and °° (P < 0.025).

stained positively for laminin M, laminin B2 (FIGS. 4a, and 4b, respectively) and laminin B1 (not shown). aminin M antibodies were not reactive with intramuscular blood vessels in control tissues (FIGS. 1a and 1i, and FIG. 4a). Intramuscular blood vessels were reactive, however, for laminin A and laminin B2 (see, for example, FIGS. 1d and 1c) and for laminin B1 (FIGS. 1b and 1j), although immunostaining of the latter is fainter and more variable. A pattern of staining similar to that observed using anti-laminin B2 antibodies was obtained when control tissues were reacted with the polyclonal anti-laminin antiserum, EHS0 (not shown).

These results indicate that laminin A is restricted to intramuscular blood vessels in control OND and other CMD muscles (FIGS. 1d and 1l, and FIG. 4c). In addition, laminin M, laminin B1 and laminin B2 subunits, but not the laminin A subunit, are clearly localized at the basal lamina of each muscle fiber. These results suggest that a heterotrimeric laminin M-B1-B2 isoform is present at the muscle fiber basal lamina.

Figures 1M, 1N, 1O, 1P:
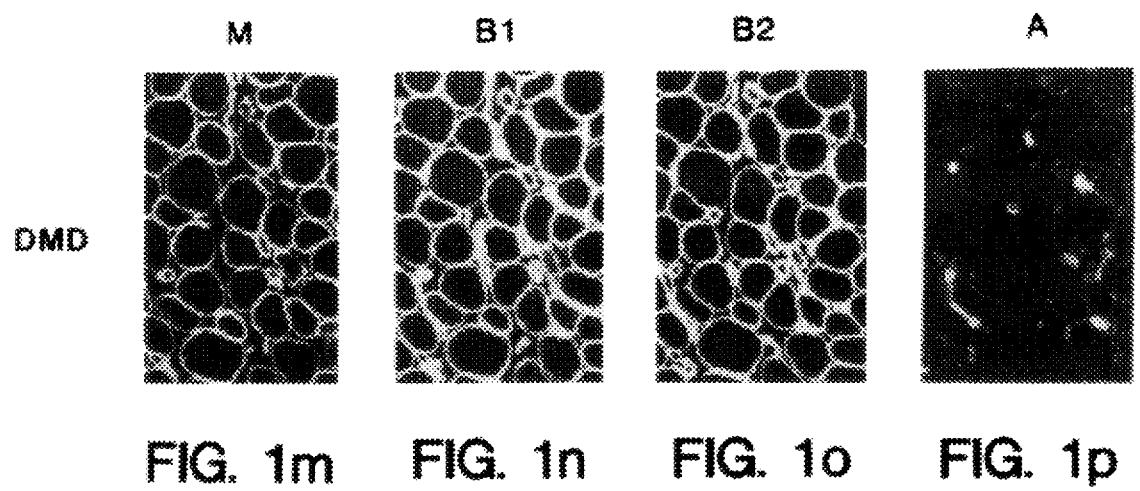

Muscle samples obtained from Duchenne muscular dystrophy (DMD) patients showed immunostaining patterns for laminin M, laminin B1 and laminin B2 that were similar to the patterns observed in OND and other CMD muscle samples. In addition, over 90% of the muscle samples from DMD patients showed an additional faint immunoreactivity with anti-laminin A antibodies (FIG. 1p). Also, whereas regenerating muscle fibers stained abnormally for spectrin (FIG. 2l), laminin M, laminin B1 and laminin B2 appeared to be well-preserved in these same fibers (FIGS. 1m, 1n and 1o, respectively).

In muscle samples obtained from FCMD patients, a dramatic reduction in the immunostaining intensity for laminin M, laminin B1 and laminin B2 was observed around each muscle fiber (FIGS. 1e, 1f and 1g, respectively). In contrast, capillary immunoreactivity appeared normal (compare FIGS. 1f and 1g).

Figures 4G, 4H, 4I:
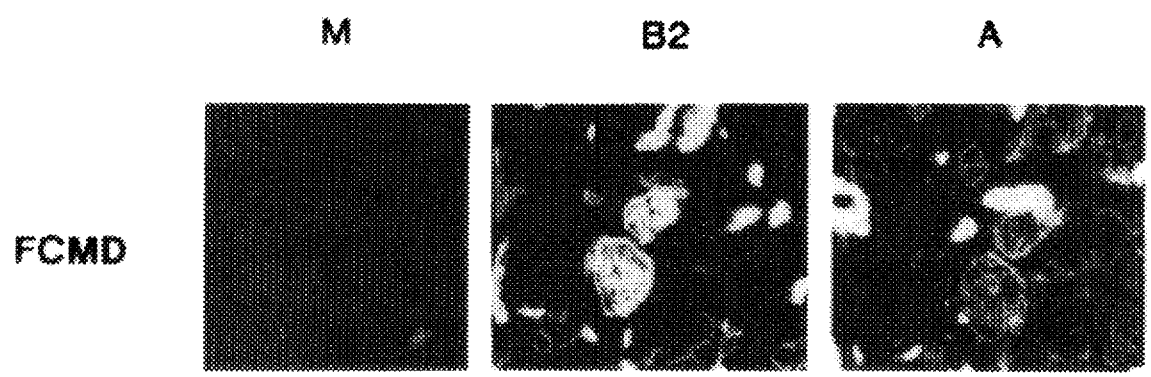
Figure 5A:
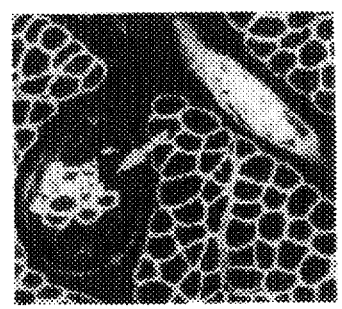
FIGS. 5.a. and 5.b. Muscle spindle (arrow) of control OND (FIG. 5a) and a patient with FCMD (FIGS. 5b and c). Although extrafusal muscle fibers are only faintly immunostained for laminin M in FCMD muscle, intrafusal spindle fibers react normally (FIG. 5b). Magnification ×215.

Immunoreactivity with the various antibodies was further characterized by quantitative analysis of the immunostaining pattern (Table 3) and the immunostaining intensity (Tables 4.a. and 4.b.). As shown in Table 4, reductions in immunostaining intensity were most obvious for muscle-specific laminin M (approximately 22% of control value by densitometric analysis) (compare, also, FIGS. 5a, 5b). In addition, one FCMD patient showed no immunoreactivity with laminin M (FIG. 4g) but was positive for laminin B1 (not shown) and laminin B2 (FIG. 4h). Furthermore, if muscle fibers having a "normal" pattern of immunostaining are considered, the FCMD muscle samples showed a significantly lower percentage of normally immunoreactive fibers for laminin M (3.1%), laminin B1 (3.9%) and laminin B2 (14.3%) as compared to other CMD (94.9%, 94.2% and 97.1%, respectively), DMD (92.5%, 93.3% and 97.8%, respectively) and OND (98.7%, 97.5% and 97.8%, respectively). Interestingly, a few histologically normal fibers were negative for laminin M in FCMD muscle.

Ehrig et al. (1990) have reported that laminin A is not present in normal adult muscles. Here, however, laminin A was observed in approximately 90% of muscle fibers obtained from FCMD and DMD patients (see FIGS. 1h, and 1p, and FIGS. 4f and 4i). Thus, at least two different heterotrimeric laminin variants (M-B1-B2 and A-B1-B2), which are not present in normal muscle, are found in FCMD and DMD muscle.

Figure 5B:
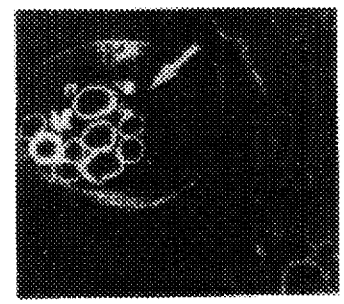
Figure 6A:
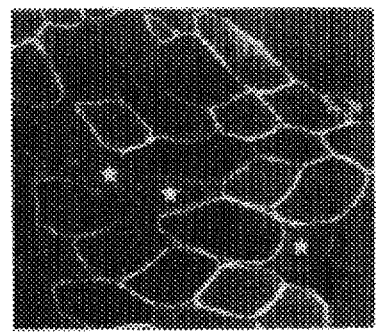
FIGS. 6.a. to 6.c. Consecutive frozen sections from a patient with DMD carrier. Immunof luorescence of dystrophin (FIG. 6a) reveals a mosaic pattern of both positive and negative fibers. Although laminin A is undetectable in normal muscle fiber, occasional dystrophin-negative fibers show positive immunostaining (asterisk) with a variable staining pattern (FIG. 6b). Laminin M stained normally in all fibers (FIG. 6c). Magnification ×250.
Figure 6B:
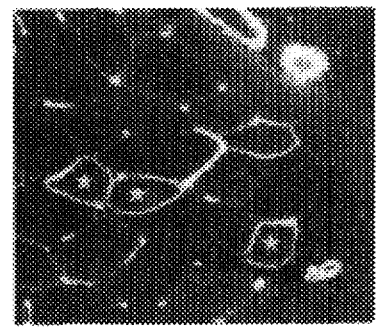
Figure 6C:
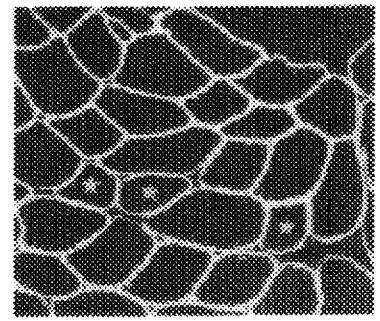

Intrafusal fibers of muscle spindle were positive for all laminin subunits. In addition, although extrafusal muscle fibers samples obtained from FCMD patients showed faint staining for laminin M, spindle fibers immunostained normally (FIG. 5b).

Figures 2A, 2B, 2C:
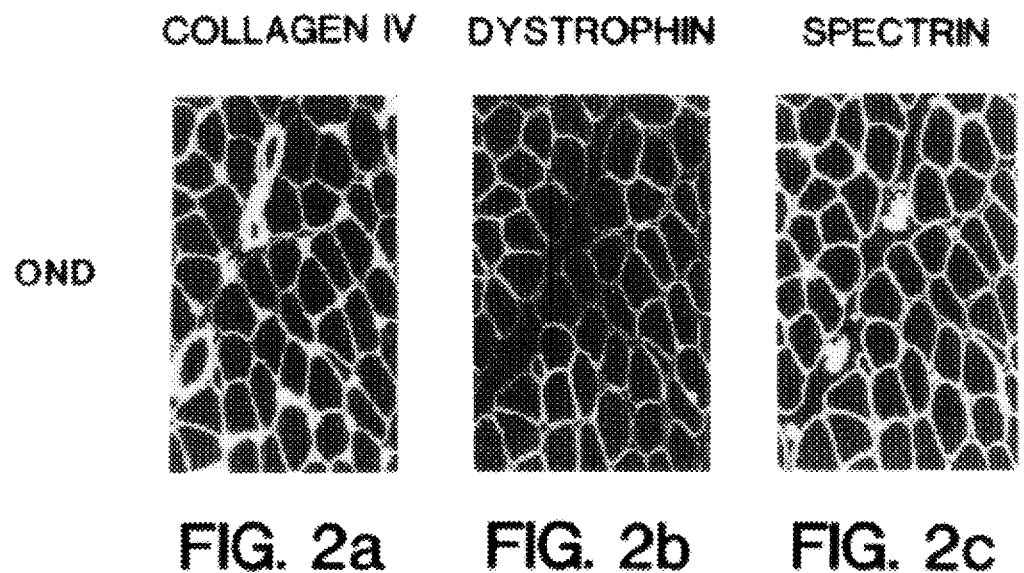
FIGS. 2.a. to 2.l. Consecutive frozen section of the same muscle samples of FIG. 1. Sections from control OND (FIGS. 2a, 2b, 2c), FCMD (FIGS. 2d, 2e, 2f), other CMD (FIGS. 2g, 2h, 2i) and DMD (FIGS. 2j, 2k, 2l) immunostained for type IV collagen (FIGS. 2a, 2d, 2g, 2j), dystrophin (FIGS. 2b, 2e, 2h, 2k) and spectrin (FIGS. 2c, 2f, 2i, 2l). In DMD muscle samples, although dystrophin is not detected (FIG. 2k), spectrin reactivity is preserved (FIG. 2l) with few disrupted, degenerating fibers observed (indicated by the asterisk). In FCMD muscle samples, abnormally immunoreacted fibers for each antibody is occasionally observed. Vascular basal lamina is equally immunostained for type IV collagen. Magnification ×215.
Figures 2D, 2E, 2F:
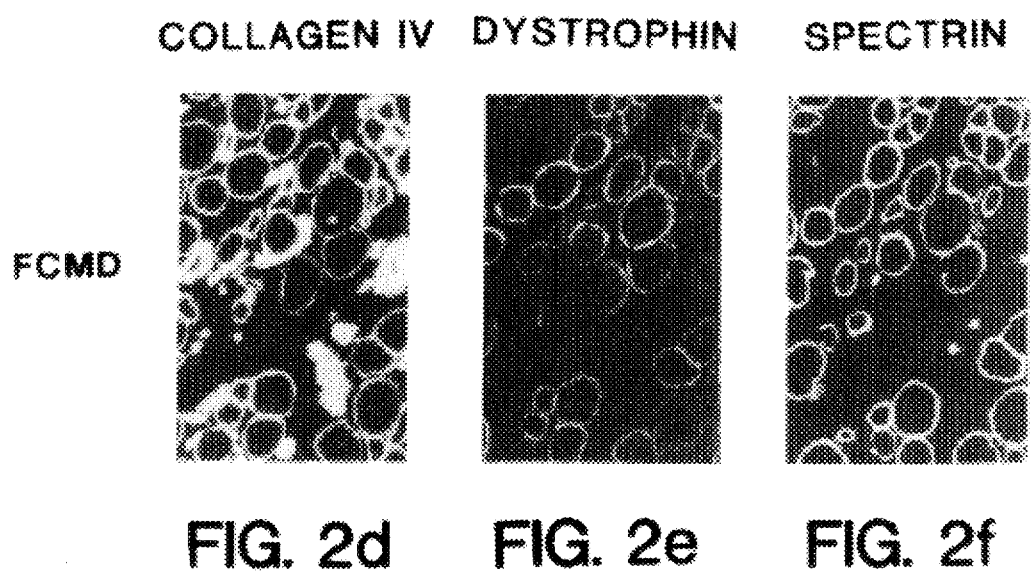
Figures 2G, 2H, 2I:
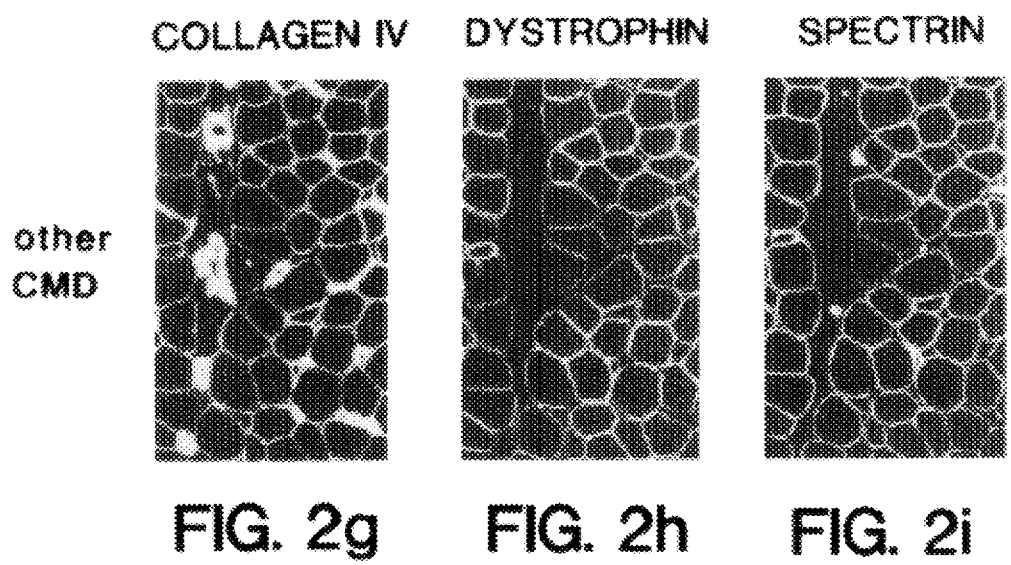
Figures 2J, 2K, 2L:
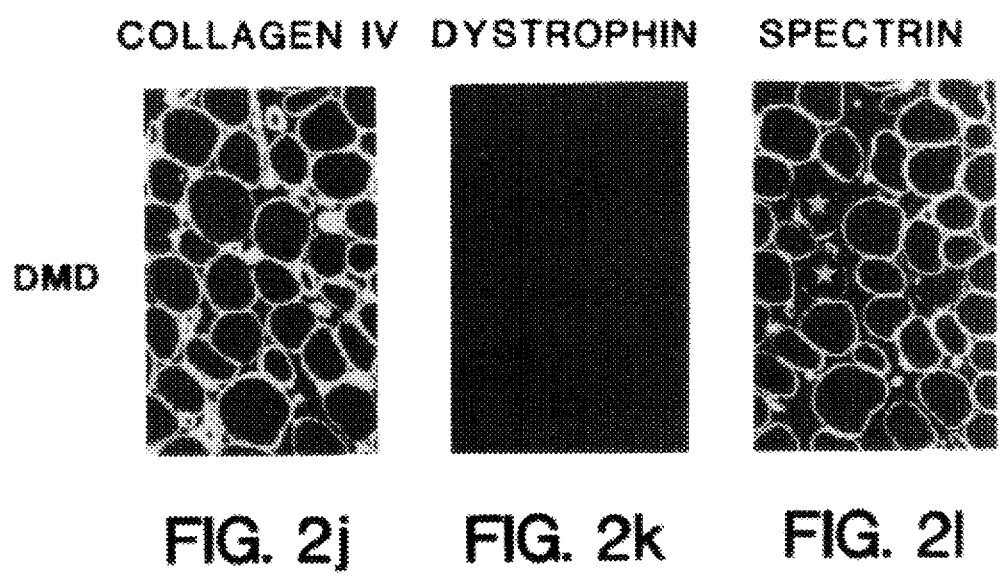

Dystrophin and spectrin:

The immunostaining patterns observed for dystrophin and spectrin were consistent with previous reports (Arikawa et al., 1991). Dystrophin was not detected in the muscle samples obtained from patients with DMD (FIG. 2k; see, also, Table 3). In muscle samples obtained from FCMD patients, occasional abnormal immunostaining patterns for dystrophin and for spectrin were observed at the plasma membrane (FIG. 2e; see, also, Table 3).

Type IV collagen:

Type IV collagen, like laminin B2, was present at the basal lamina of all control muscle fibers and blood vessels. Although the staining intensity of type IV collagen in FCMD muscle was not significantly different from other diseases (FIG. 3 and Tables 4.a. and 4.b.), FCMD muscle showed a higher percentage of fibers with an abnormal pattern of immunostaining (approximately 83% faint and/or blurred) as compared to other CMD (12%), DMD (12%) and OND (2%) (see Table 3, collagen IV).

EXAMPLE III

DIAGNOSTIC SCREENING FOR INDIVIDUALS PREDISPOSED TO FUKUYAMA'S DISEASE

This example demonstrates the utility of various methods for screening a population to identify those individuals having an altered expression and localization of laminin M protein or altered expression of M chain mRNA and, therefore, predisposed to exhibiting the symptoms of Fukuyama's disease. Similar methods are useful for identifying an individual predisposed to a muscular dystrophy such as WWS and MEB, which can have the same genetic defect observed for FCMD.

Screening for altered expression and localization of laminin M protein:

A muscle tissue sample can be obtained by biopsy and screened by comparing the test sample with a control sample as described above. Altered expression and localization of laminin M is considered diagnostic of an individual predisposed to a congenital muscular dystrophy such as Fukuyama's disease.

Figure 7A:
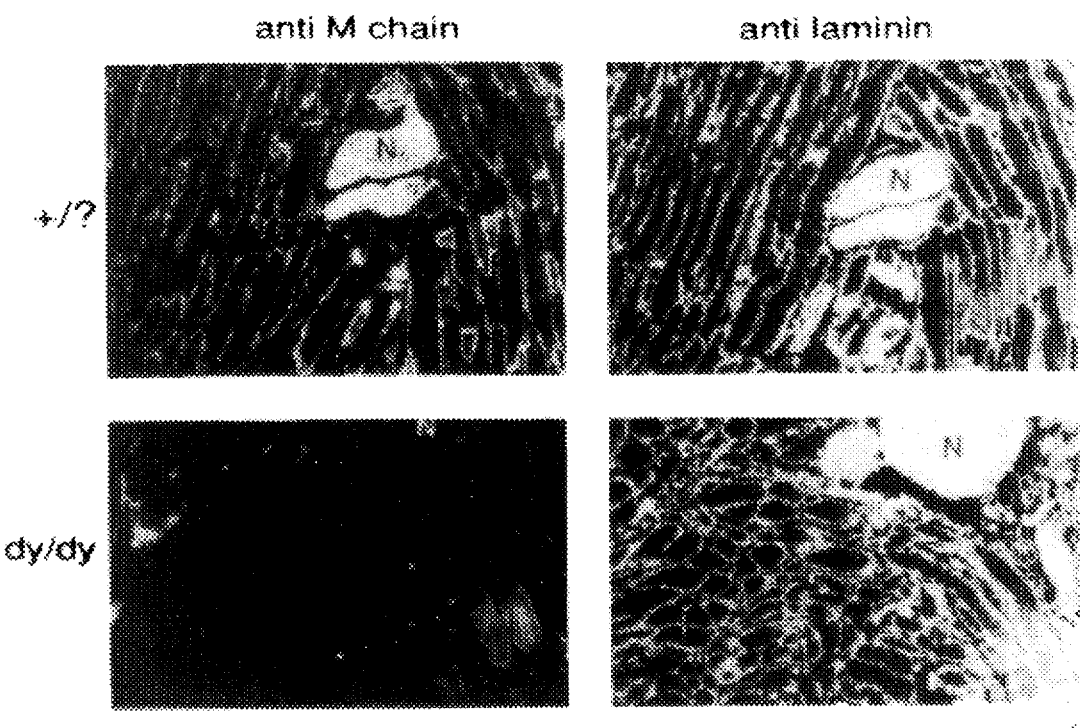
FIGS. 7.a. and 7.b. Immunofluorescence photomicrographs of a 9 week human placenta stained with anti-laminin M antibody. Laminin M protein staining is apparent in the trophoblast basement membranes, whereas the trophoblast cells, themselves, as well as the few blood vessels in the field are negative. Some stroma fibril staining also appears.
Figure 7B:
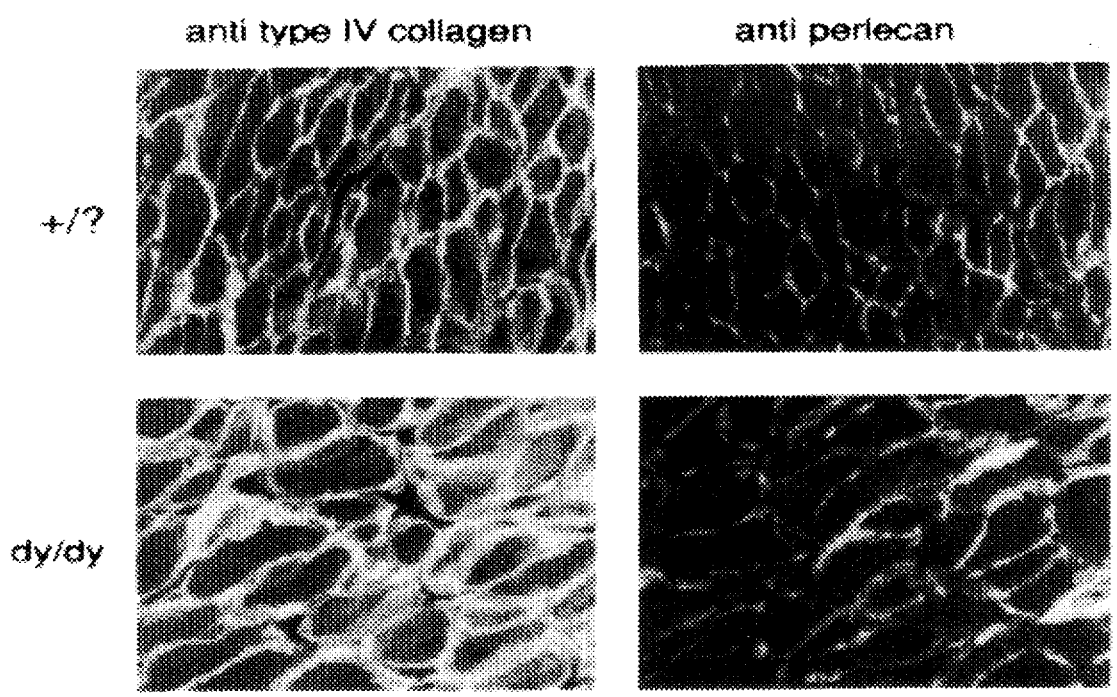

The screening procedure is particularly useful as a method of prenatal diagnosis. For prenatal diagnosis, a sample of placenta tissue can be obtained, for example, by needle biopsy. The test sample can be prepared as described above and compared with a control sample. FIG. 7 shows the immunostaining observed in a sample obtained from a normal 9 week human placenta (FIGS. 7a and 7b). Placenta tissue was dissected from a clinically aborted 9 week old fetus and frozen. Tissue sections were prepared as described in Example I and the sections were incubated with the 2G9 anti-laminin M monoclonal antibody as described. Following incubation of the sample with the 2G9 antibody, the sections were incubated with an FITC-labelled second antibody.

As shown in FIG. 7, immunostaining of laminin M is observed in the trophoblast basement membranes. A minimal level of positive immunostaining also is observed in some stroma fibrils. However, the trophoblast cells, themselves, and blood vessels present in the field do not immunostain for laminin M. These results indicate that the expression and localization of laminin M in normal human placenta is similar to the expression and localization observed in normal muscle tissue. Thus, normal placenta can be compared with test samples obtained from placenta to identify individuals having altered expression and localization of laminin M.

Screeninq for expression of mRNA encoding the M chain of laminin M:

A muscle tissue sample or a placenta sample can be obtained from an individual to be tested as described above. RNA can be isolated from the tissue using standard extraction methods as described below (see, also, Sambrook et al., 1989). If desired, poly A$^+$ RNA also can be isolated (see Example VI).

The level of expression of M chain mRNA in a tissue sample obtained from an individual can be determined using northern blot analysis or, if greater sensitivity is required, by PCR analysis. The methods for performing these analyses are well known in the art and described in detail in Example VI, below, and by Engvall et al. (1992). Diagnostic M chain mRNA assays are performed by analyzing a test sample in parallel with a control sample, which expresses a normal level of M chain mRNA. Such a control sample is matched to the test sample based, for example, on the age and sex of the individual being tested. Using this diagnostic screening assay, an individual who is predisposed to FCMD can be identified by detecting a decreased expression of M chain mRNA as compared to the expected normal level of M chain mRNA expression.

EXAMPLE IV

METHODS FOR ANALYZING PROTEIN EXPRESSION IN MOUSE TISSUE SAMPLES

This example describes methods for examining the expression and localization of cytoskeleton/basal lamina proteins in mouse tissue samples. The results obtained using these methods are described in Example V, below.

Animals:

Homozygous (dy/dy) and control (+/? and +/+) 129 B6F1/ J-dy mice were purchased from Jackson Laboratories ("?" indicates the mice are +/+ or +/dy). Wistar rats were bred in the animal facility of La Jolla Cancer Research Foundation.

Antibodies:

Three different M chain-specific polyclonal antibodies were used. One anti-M chain antibody was an affinity purified rabbit antibody specific for the 60 kiloDalton (kDa) fragment at the carboxy terminus of the human laminin M chain. This fragment contains repeats 4 and 5 in the G domain, which is present in laminin heavy chains but absent in the lighter chains (Leivo and Engvall, 1988). A second anti-M chain antibody consisted of antiserum specific for a sequence present in the second repeat in the G domain (Ehrig et al., 1990). The third anti-M chain antibody consisted of an antiserum raised against the 300 kDa amino terminus of mouse M chain (Paulsson et al., J. Biol. Chem. 266:17545–17551 (1991), which is incorporated herein by reference).

Polyspecific antisera to rat laminins and to human laminins were prepared as described by Engvall et al., Arch. Biochem. Biophys. 222:649–656 (1983), which is incorporated herein by reference, and by Ehrig et al. (1990). These polyspecific antisera react with several laminin subunits. A rabbit antiserum to mouse type IV collagen was prepared as described by Engvall et al., Cell 29:475–482 (1982), which is incorporated herein by reference. Monoclonal rat antibodies to perlecan and entactin were prepared using the method described by Ljubimov et al., Int. J. Cancer 50:552–556 (1992), which is incorporated herein by reference. Antiserum specific for mouse fibronectin was prepared as described by Ruoslahti et al., Meth. Enzymol. 82:803–831 (1982), which is incorporated herein by reference.

Immunofluorescence:

Mouse skeletal muscle and heart were collected, embedded in O.C.T. embedding medium (Miles Laboratories), and frozen immediately in 2-methylbutane at −70° C. Frozen tissue sections (10–20 µm) were cut on a cryostat and fixed in ice cold acetone for 10 min. Sections were incubated with primary antibodies at 1:50 to 1:200 dilution for 2 hr at 37° C. After washing with PBS three times, the sections were incubated with fluorescein isothiocyanate-(FITC-) conjugated goat anti-rabbit IgG or anti-mouse IgG at 37° C. for 1 hr. The sections were mounted with 20% glycerol and examined under a Zeiss fluorescence microscope.

Transmission electron microscopy:

Specimens of stretched and unstretched leg muscle from 8 week old normal and dystrophic mice were fixed in 70% Karnovsky's fixative, rinsed in 0.1M cacodylate buffer, pH 7.2, postfixed in 1% $OsO_4$ in cacodylate buffer, and treated with 1% tannic acid, pH 7.0, as described by Simionescu and Simionescu, J. Cell Biol. 70:608–621 (1976), which is incorporated herein by reference. The tissue samples were rinsed in 1% $Na_2SO_4$ and 0.1M cacodylate buffer, then embedded in Epon. Ultrathin sections were stained with uranyl acetate and lead citrate and examined with a Phillips 201 electron microscope.

SDS-PAGE Immunoblotting:

Laminins were extracted from tissue samples as described by Paulsson et al. (1991). Briefly, frozen tissue samples were thawed and immediately homogenized (0.1 g wet weight of tissue/ml) in extraction buffer (0.15M NaCl, 0.05M Tris-HCl, pH 7.4, containing 2 mM phenylmethylsulfonylfluoride and 2 µg/ml aprotinin) at 4° C. using a Polytron homogenizer. The homogenate was centrifuged at 16.000×g for 15 min and the supernatant discarded. The tissue residue was resuspended in 2 vol of extraction buffer containing 10 mM EDTA, incubated for 1 hr with frequent mixing, then centrifuged as described above. The protein content of the EDTA extracts was estimated using the BCA assay (Pierce). Aliquots of the EDTA extracts were fractionated under reducing conditions by sodium dodecyl sulfate-polyacrylamide gel electrophoresis (SDS-PAGE) using 4–12% gradient gels (Novex) and high molecular weight markers (Gibco). Proteins were electrophoretically transferred to Immobilon PVDF filters (Millipore) and processed for immunoblotting as described by Leivo and Engvall (1988). Affinity purified antibodies were added at 3 µg/ml. Alternatively, anti-M chain antisera were added at a 1:500 dilution. Immunoreactive protein bands were visualized using the enhanced chemiluminescence method (Amersham).

EXAMPLE V

EXPRESSION OF BASAL LAMINA/ CYTOSKELETON PROTEINS IN MOUSE TISSUE SAMPLES

This example describes the results of experiments demonstrating that the molecular abnormalities associated with the muscular dystrophy observed in dy/dy mouse are similar to the defects observed in Fukuyama's Congenital Muscular Dystrophy (FCMD) in humans.

As shown in FIG. 8.a., histologic sections of skeletal muscle and peripheral nerve obtained from homozygous dy/dy mouse contained no laminin M when analyzed by indirect immunofluorescence using affinity purified anti-M chain antibodies. In comparison, sex-matched heterozygous or wild type littermates of the dy/dy mice (FIG. 8.a.), as well as samples obtained from other strains of mice (not shown), contained normal laminin M protein expression.

The dy/dy mice showed normal expression and localization of other basement membrane components as evidenced by staining with a polyspecific antiserum against laminins (FIG. 8.a.), with antiserum against type IV collagen (FIG. 8.b.) and with monoclonal antibodies specific for the heparan sulphate proteoglycan, perlecan, (FIG. 8.b.) and entactin (not shown). Examination of tissue sections from other organs including heart and testis also showed that the dy/dy mice lack laminin M in these tissues (not shown).

In order to study the muscle basement membrane in more detail at high resolution, muscle tissue samples were examined using transmission electron microscopy. In normal mice, the basement membrane has a continuous appearance (FIG. 9A). In contrast, significant abnormalities were detectable in the basement membrane of dy/dy muscle (FIGS. 9B–9D). In particular, the basement membrane in the dystrophic mice was variable in appearance and was thin, fragmented and, in some cases, completely absent.

Figures 10A, 10B:
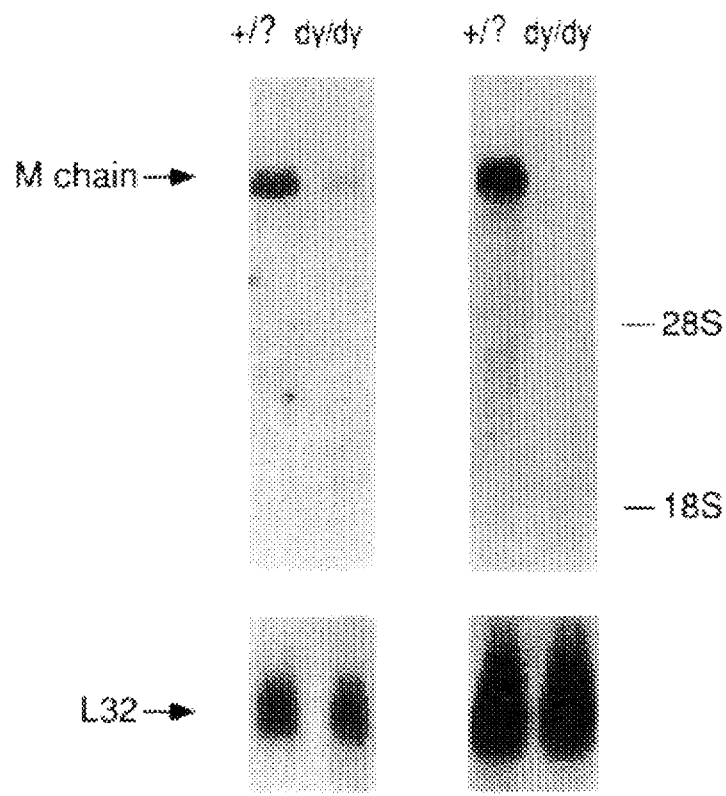
(FIG. 10a) Antiserum against the 300 kDa N-terminal segment of the M chain of laminin M.
(FIG. 10b) Affinity purified antibodies to the C-terminal segment of the M chain.

The structure of the laminins in the muscle of dy/dy mice was further analyzed by immunoblot analysis. In normal tissue, the M chain in laminin M is processed into two major fragments of 300 kDa and 80 kDa (Ehrig et al., 1990). As expected, in muscle samples obtained from normal or heterozygous +/dy mice, the anti-300 kDa antiserum (FIG. 10.a.) and the anti-peptide antiserum (not shown) detected the 300 kDa amino terminal fragment of the M chain and the affinity purified antibody to the carboxy terminal segment of the M chain detected the 80 kDa fragment (FIG. 10.b.). In contrast, none of the three M chain-specific antisera detected the presence of laminin M in samples obtained from a dy/dy mouse (FIGS. 10a–10b; anti-peptide antiserum not shown).

Polyspecific antiserum, which was raised against human laminin from placenta, reacts with several of the laminin heavy chains, including A and M, and the laminin light chains, including B1, B2 and S. The polyspecific antiserum detected protein bands having apparent molecular weights of 400, 300 and 200 kDa in samples obtained from non-dystrophic (+/?) mice (FIG. 10.c.). These are the expected molecular weights for the A chain, the amino terminal segment of the M chain and the B1/B2/S chains, respectively. In samples obtained from dystrophic mice, the polyspecific antiserum detected bands of 400 kDa and 200 kDa, but not 300 kDa (FIG. 10.c.). These results confirm the absence of the M chain, but not the A and B chains, in dy/dy mice. Anti-fibronectin antiserum detected the presence of fibronectin in approximately equal amounts in samples obtained from normal and dystrophic mice (not shown).

The results of these experiments indicate that muscular dystrophy in the dy/dy mouse is characterized by decreased levels of expression of laminin M protein. Thus, the form of muscular dystrophy found in dy/dy mice is characterized by the same molecular defect that was described in FCMD patients (see Example II, above).

EXAMPLE VI

NUCLEIC ACID ANALYSIS IN dy/dy MICE

This example demonstrates that the decreased expression of laminin M protein in dy/dy mice is associated with decreased expression of mRNA encoding the M chain of laminin M.

mRNA analysis:

The expression of mRNA encoding the M chain of laminin M was determined using northern blot analysis and PCR analysis. Total RNA was isolated from skeletal muscle of 15 day old rats using acid guanidinium thiocyanate-phenol/chloroform extraction. Poly $A^+$ RNA was purified from skeletal muscle of 4 week old mice (+/? and dy/dy) using the Fast Track mRNA isolation kit (Invitrogen) as described by the manufacturer.

For northern blot analysis, 30 µg of total RNA obtained from leg muscle of 4 week old normal and dystrophic mice or from heart of 5 week old normal and dystrophic mice was separated by electrophoresis in a 0.9% agarose/formaldehyde gel (Sambrook et al., 1989). Following electrophoresis, the RNA was nicked by treating the gel with a UV crosslinker (Stratagene) and the RNA was transferred to Hybond N filters (Amersham) and fixed to the filters by heating at 80° C. for 2 hr.

A $^{32}$P-labeled 3 kilobase (kb) cDNA sequence that corresponds to the 3' end of the human M chain cDNA (Ehrig et al. (1990)) was used for hybridization. The cDNA sequence was radiolabelled using random primers and α-$^{32}$P-dCTP. Approximately $2 \times 10^7$ cpm/ml of the labelled probe (specific activity $10^9$ cpm/pg) was added to the filter and hybridization was allowed to proceed overnight at 42° C. in a buffer containing 50% formamide, 5× SSC, 5× Denhardt's solution, 100 µg/ml herring sperm DNA and 7% dextran sulfate (20× SSC is 175.3 g NaCl and 88.2 g sodium citrate/liter, pH 7.0; 50× Denhardt's solution is 5 g Ficoll (Type 400; Pharmacia), 5 g polyvinylpyrrolidone and 5 g bovine serum albumin (Fraction V; Sigma)/500 ml). Following hybridization, the filter was washed twice at a final stringency of 1× SSC, 0.1% SDS at 50° C. for 20 min, then was exposed to Kodak XAR film with intensifying screen for 4 hr at −70° C.

Figure 11:
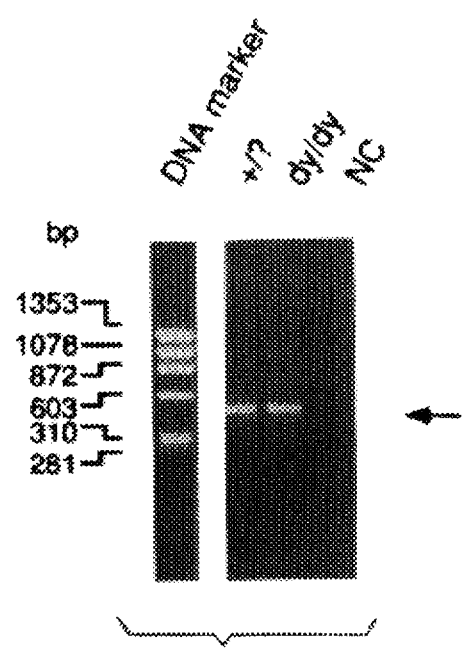
FIG. 11a–11b. Northern blot analysis of 30 µg of total RNA obtained from leg muscle of 4 week old normal and dystrophic mice (FIG. 11a) and from heart of 5 week old normal and dystrophic mice (FIG. 11b). The approximately 10 kb M chain mRNA was greatly reduced in leg muscle and undetectable in heart of dystrophic mice as compared to normal mice. The mRNA level for ribosomal protein L32 was determined for each sample to show that approximately equal amounts of RNA were loaded in each lane of FIG. 11a and in each lane of FIG. 11b. Migration of 18S and 28S ribosomal RNA is indicated.

As shown in FIG. 11, normal mice produce M chain mRNA that is approximately 10 kb in size. In contrast, the M chain mRNA band was absent or greatly reduced in the dystrophic mice (FIGS. 11a. and 11b; dy/dy). In order to determine whether a very low level of M chain mRNA was being expressed, PCR was used as a more sensitive method for detecting mRNA expression. Poly $A^+$ RNA obtained from skeletal muscle of normal or dystrophic mice was reverse transcribed and amplified using the primers and method described by Engvall et al. (1992). Amplification using PCR primers that hybridize within the first repeat in the G domain resulted in a product of the expected size in both dy/dy mice and normal mice (FIG. 12; arrow). This result demonstrates that M chain mRNA is expressed in dy/dy mice, albeit at very low levels as indicated by northern blot analysis. These results demonstrate that the decreased expression of laminin M protein observed in dy/dy mice reflects an abnormally low expression of M chain mRNA in these mice.

Southern blot analysis:

In order to determine whether decreased M chain mRNA expression is due to a gross defect in the gene encoding the M chain of laminin M, Southern blot analysis was performed. Genomic DNA was isolated from the liver of 4 week old normal or dy/dy mice (Sambrook et al., 1989). Ten µg samples of genomic DNA were incubated overnight at 37° C. with 100 units of either HindIII, BamHI, EcoRI, PstI or XbaI restriction endonuclease, then separated by electrophoresis on a 0.7% agarose gel, nicked using UV treatment, as described above, and transferred to Hybond N filters.

A 458 base pair rat M chain cDNA sequence, which is equivalent to residues 501 to 969 in the human M chain cDNA (Ehrig et al., 1990), was radiolabelled as described above. Approximately $1 \times 10^7$ cpm/ml of the labelled probe (specific activity $6 \times 10^8$ cpm/µg) was added to the filter and incubated at 42° C. overnight in a buffer containing 50% formamide, 5× SSC, 5× Denhardt's solution and 100 µg/ml herring sperm DNA. Following hybridization, the filter was washed at a final stringency of 0.1× SSC, 0.1% SDS at 50° C. for 50 min and was exposed to Kodak XAR film with intensifying screen for 17 hr at −70° C.

No differences were observed in the restriction fragment patterns of homozygous (dy/dy), heterozygous and wild type mice (not shown). Thus, the altered expression of M chain mRNA and of laminin M protein expression observed in the dy/dy mice are not due to gross defects such as major deletions in the laminin M gene in dy/dy mice.

EXAMPLE VII
USE OF dy/dy MICE FOR IDENTIFYING AGENTS USEFUL FOR TREATING FCMD PATIENTS

This example describes the use of dy/dy mice in a screening assay for identifying effective therapeutic agents such as drugs that can reduce or prevent the clinical symptoms associated with FCMD.

The dy/dy mouse provides a useful model system for identifying effective therapeutic agents for treating FCMD patients. Both FCMD in humans and the dy/dy-related muscular dystrophy in mice are inherited in an autosomal recessive manner and, as described above, the altered expression of laminin M protein, which is characteristic of FCMD in humans, also occurs in dy/dy mice. In addition, the dy gene locus in the mouse is linked to the gene encoding the dystrophin related protein (DRP) present on chromosome 10 in the mouse. Similarly, in humans, the gene encoding the M chain of laminin M is linked to the DRP gene on chromosome 6, which is homologous to mouse chromosome 10 (Buckle et al., Hum. Genet. 85:324-326 (1990)). Thus, the same genetic defect appears to be responsible for FCMD in humans and dy/dy-related muscular dystrophy in mice.

Screening assays can utilize normal and dystrophic dy/dy mice and a potentially effective agent can be administered in a range of doses. Treatment with the agent can be for various periods of time and, if desired, an agent can be administered more than once.

Initial assays will determine the effectiveness of an agent for prolonging the stamina of dy/dy mouse on a treadmill. An agent can be administered to the mouse and, after various periods of time, the length of time the mouse can continue running on the treadmill can be determined. The time of a treated mouse can be compared to an untreated mouse. In addition, before treatment, the time a dystrophic mouse can run on the treadmill can be determined, then compared with the time after a potentially effective agent is administered to the mouse. Appropriate control experiments will be performed and statistically significant results can be obtained using well known methods of experimental design.

An effective agent also can be identified by obtaining a sample of a tissue from a treated mouse following exercise and determining the level of expression of a factor involved in an inflammatory-type response. Tissue samples can be obtained and prepared for immunohistological analysis as described above. The level of TGFβ in tissue sample can be determined by immunofluorescence microscopy using an FITC-labelled anti-TGFβ antibody or a labelled second antibody as described above. Anti-TGFβ antibodies and antibodies to other growth factors or cytokines and appropriate second antibodies can be obtained from commercial sources. Comparison of immunofluorescence intensity in a treated dystrophic mouse and an untreated mouse can identify an agent that effectively reduces or prevents increased TGFβ levels.

Although the invention has been described with reference to the examples provided above, it should be understood that various modifications can be made without departing from the spirit of the invention. Accordingly, the invention is limited only by the following claims.

We claim:

1. A method to aid in the identification of an individual predisposed to an autosomal recessive muscular dystrophy, comprising the steps of:
   a. obtaining a tissue sample from an individual suspected of being predisposed to the autosomal recessive muscular dystrophy, said tissue sample obtained from a tissue known to express laminin M in a subject not predisposed to said autosomal recessive muscular dystrophy;
   b. contacting said tissue sample with at least one antibody, said antibody which specifically binds to at least one component of basal lamina, said component selected from the group consisting of a laminin and a laminin subunit, said laminin subunit being A, M, B1, B2 or S, under conditions sufficient to effect specific binding of said antibody; and
   c. detecting a level and/or localization of said specific binding, which, when compared to a normal level and/or localization of specific binding, indicates that said individual is predisposed to said autosomal recessive muscular dystrophy.

2. The method of claim 1, wherein said individual is a fetus and said method is performed prenatally.

3. The method of claim 1, wherein said at least one component is laminin M.

4. The method of claim 1, wherein said autosomal recessive muscular dystrophy is Fukuyama's congenital muscular dystrophy.

5. The method of claim 4, wherein said at least one component is laminin M.

6. The method of claim 1, wherein said at least one antibody is detectably labeled.

7. The method of claim 1, wherein said tissue sample is muscle or placenta.

\* \* \* \* \*